(12) United States Patent
Li et al.

(10) Patent No.: US 7,371,364 B2
(45) Date of Patent: May 13, 2008

(54) CYCLIC PEPTIDE AND IMAGING COMPOUND COMPOSITIONS AND USES FOR TARGETED IMAGING AND THERAPY

(75) Inventors: Chun Li, Missouri City, TX (US); Wei Wang, Sugar Land, TX (US); Shi Ke, Missouri City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 197 days.

(21) Appl. No.: 10/918,009

(22) Filed: Aug. 13, 2004

(65) Prior Publication Data

US 2005/0069494 A1 Mar. 31, 2005

Related U.S. Application Data

(60) Provisional application No. 60/495,658, filed on Aug. 15, 2003.

(51) Int. Cl.
| | |
|---|---|
| *A61K 51/00* | (2006.01) |
| *A61K 38/00* | (2006.01) |
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |

(52) U.S. Cl. .................... 424/1.69; 514/9; 530/317
(58) Field of Classification Search ............... None
See application file for complete search history.

(56) References Cited

FOREIGN PATENT DOCUMENTS

| WO | 93/12819 | 7/1993 |
|---|---|---|
| WO | 9312819 | 7/1993 |
| WO | 97/47750 | 9/1999 |
| WO | 9947550 | 9/1999 |
| WO | 02/076451 | 10/2002 |
| WO | 02076451 | 10/2002 |

OTHER PUBLICATIONS

International Search Report PCT/US2004/026220.
Erkki Koivunen et al., "Tumor targeting with a selective gelatinase inhibitor," Nature Biotechnology, vol. 17, pp. 768-774, Aug. 1999.
Peter C. Brooks et al., "Requirement of Vascular Integrin $\alpha_v\beta_3$ for Angiogensis," Science, vol. 264, pp. 569-571, Apr 22, 1994.

(Continued)

*Primary Examiner*—Cecilia J Tsang
*Assistant Examiner*—Marcela M Cordero Garcia
(74) *Attorney, Agent, or Firm*—Baker Botts L.L.P.

(57) ABSTRACT

The present invention relates to novel cyclic peptides that may be conjugated with imaging agents, including novel imaging agents. Specifically, it includes c(KRGDf; SEQ ID NO. 3) NIR imaging compositions and novel cyclic HWG-FTL (SEQ ID NO. 5) polypeptides which may be used inter alia in NIR, MRI and nuclear imaging as well as therapy. Additionally, the invention includes novel imaging agents, such as TS-ICG derivatives. The invention also relates to methods of making and using such compounds. Such uses include both pre-operative and intraoperative detection of tumor cells and treatment monitoring.

39 Claims, 35 Drawing Sheets
(18 of 35 Drawing Sheet(s) Filed in Color)

OTHER PUBLICATIONS

Martin Friedlander et al., "Definition of Two Angiogenic Pathways by Distinct $\alpha_v$ Integrins," Science, vol. 270, pp. 1500-1502, Dec. 1, 1995.

Renata Pasqualini et al., "αv Integrins as receptors for tumor targeting by circulating ligands," Nature Biotechnology, vol. 15, pp. 542-546, Jun. 1997.

Dorothy A. Sipkins et al., "Detection of tumor angiogenesis in vivo by $\alpha_v\beta_3$-targeted magnetic resonance imaging," Nature Medicine, vol. 4, No. 5, pp. 623-626, May 1998.

Giampietro Gasparini et al., "Vascular Integrin: A New Prognostic Indicator in Breast Cancer," Clinical Cancer Research, vol. 4, pp. 2625-2634, Nov. 1998.

Brian P. Eliceiri et al., "The role of αv integrins during angiogenesis: insights into potential mechanisms of action and clinical development," The Journal of Clinical Investigation, vol. 103, No. 9, pp. 1227-1230, May 1999.

Roland Haubner et al., "Radiolabeled $\alpha_v\beta_3$ Integrin Antagonists: A New Class of Tracers for Tumor Targeting," The Journal of Nuclear Medicine, vol. 40, No. 6, pp. 1061-1071, Jun. 1999.

John C. Gutheil et al., "Targeted Antiangiogenic Therapy for Cancer Using Vitaxin: A Humanized Monoclonal Antibody to the Integrin αvβ3," Clinical Cancer Research, vol. 6, pp. 3056-3061, Aug. 2000.

C. Chandra Kumar et al., "Inhibition of Angiogenesis and Tumor Growth by SCH221153, a Dual αvβ3 and αvβ5 Integrin Receptor Antagonist," Cancer Research, vol. 61, pp. 2232-2238, Mar. 1, 2001.

Roland Haubner et al., "Noninvasive Imaging of αvβ3 Integrin Expression Using F-labeled RGD-containing Glycopeptide and Positron Emission Topography,:" Cancer Research, pp. 1781-1785, Mar. 1, 2001.

Oula Penate Medina et al., "Binding of Novel Peptide Inhibitors of Type IV Collagenases to Phospholipid Membranes and Use in Liposome Targeting to Tumor Cells in Vitro," Cancer Research, pp. 3978-3985, May 15, 2001.

Niels Reinmuth et al., "αvβ3 Integrin Antagonist S247 Decreases Colon Cancer Metastasis and Angiogenesis and Improves Survival in Mice,"Cancer Research, vol. 63, pp. 2079-2087, May 1, 2003.

Invitation to pay additional fees for PCT/US2004/026220, Jan. 10, 2005.

International Search Report and Written Opinion PCT/US2004/026220, 17 pages.

Transmittal of Copy of International Preliminary Report on Patentability; PCT/US2004/026220; pp. 10, Mailing Date Mar. 2, 2005.

E. Koivunen et al.; "Tumor Targeting with a Selective Gelatinase Inhibitor"; Nat/ure Biotechnology, vol. 17; pp. 768-774, Aug. 1999.

Oula Penate Medina et al.; "Binding of Novel Peptide Inhibitor of Type IV Collagenases to Phospholipid Membranes and use in Liposome Targeting to Tumor Cells in Vitro"; Cancer Research, American Association For Cancer Research, vol. 61; pp. 3978-3985, May, 15, 2001.

c(CTTHWGFTLC)
IC$_{50}$: 22.4 μM

FIGURE 1 - PRIOR ART

Bright Light
NIR
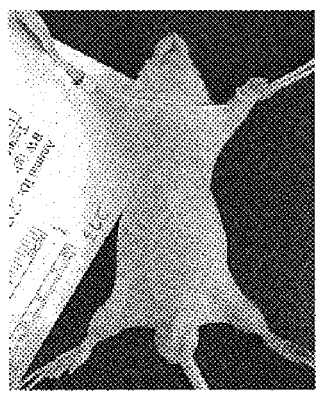
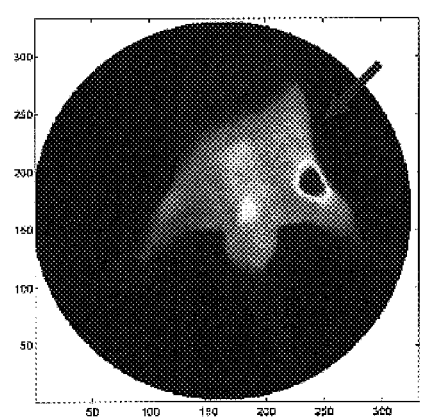
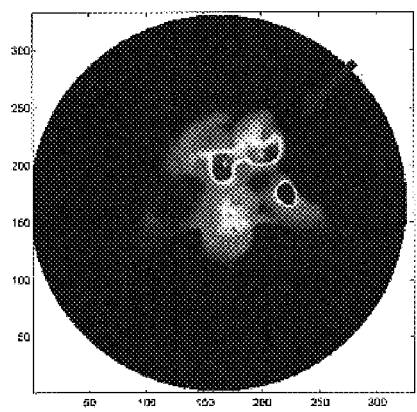
FIGURE 4A
FIGURE 4B

A     B
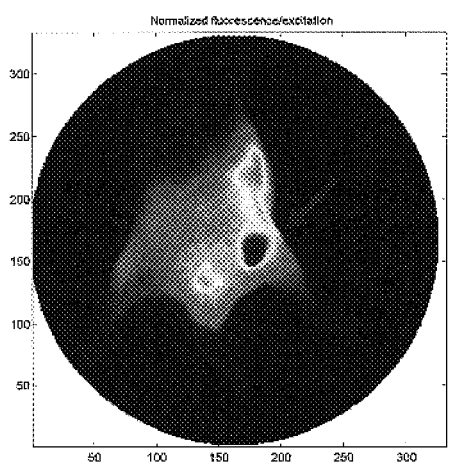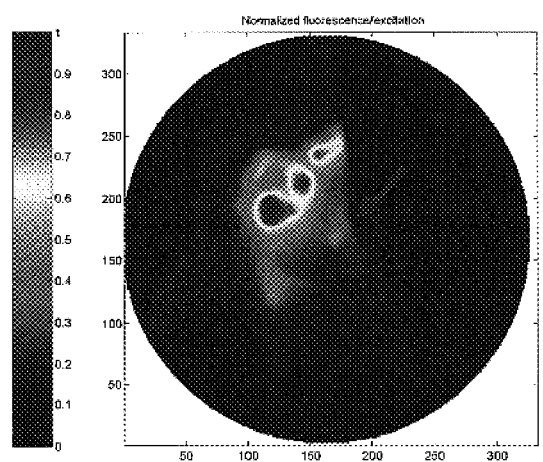
FIGURE 6

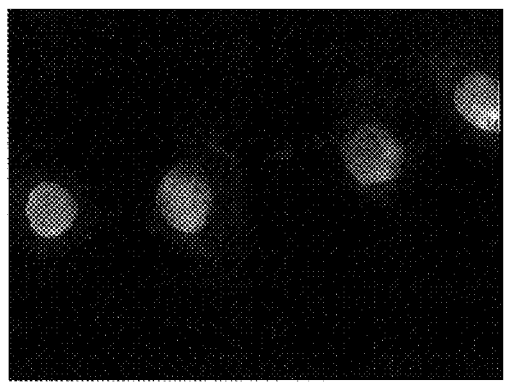 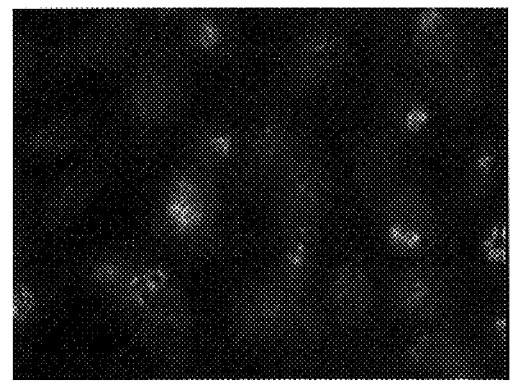
FIGURE 12

Cy5.5-c(KAHWGFTLD)NH₂    Cy5.5-c(KHGLTWFAD)NH₂
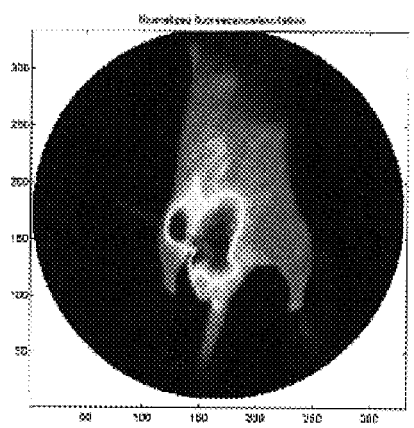 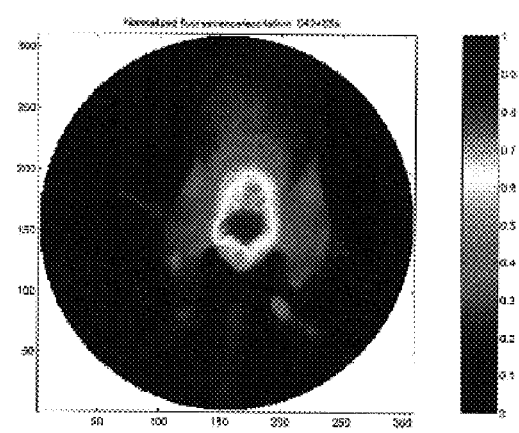
FIGURE 18

TS-ICG-c(KRGDf)          TS-ICG-(KRGDf)$_2$
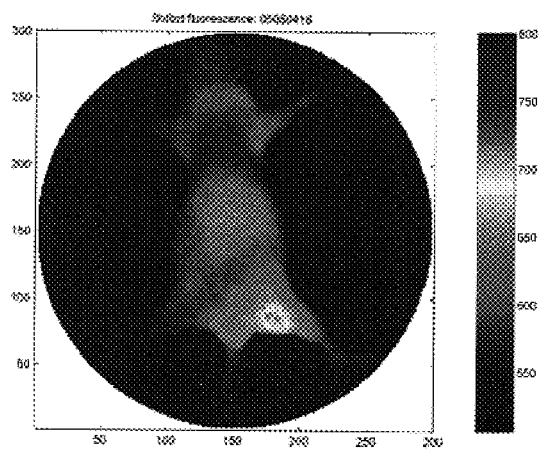
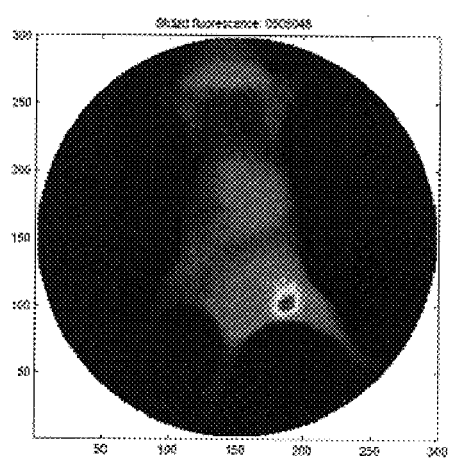
FIGURE 23

SEQUENCE LISTING

<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Peptide

<400> SEQUENCE: 1

Cys Leu Thr Phe Gly Trp His Thr Thr Cys

```
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide

<400> SEQUENCE: 2

Ala Leu Thr Phe Gly Trp His Thr Thr Ala
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Peptide

<400> SEQUENCE: 3

Phe Asp Gly Arg Lys
1               5

<210> SEQ ID NO 4
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (1)...(10)
<223> OTHER INFORMATION: Xaa = Any Amino Acid

<400> SEQUENCE: 4

Xaa Leu Thr Phe Gly Trp His Xaa Xaa Xaa
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Peptide

<400> SEQUENCE: 5

Leu Thr Phe Gly Trp His
1               5

<210> SEQ ID NO 6
<211> LENGTH: 10
<212> TYPE: PRT
<213> ORGANISM: Artificial Sequence
<220> FEATURE:
<223> OTHER INFORMATION: Peptide

<400> SEQUENCE: 6

Ala Leu Thr Phe Gly Trp His Ala Thr Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Peptide
```

```
<400> SEQUENCE: 7

Asp Leu Thr Phe Gly Trp His Thr Thr Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Peptide

<400> SEQUENCE: 8

Asp Leu Thr Phe Gly Trp His Thr Thr Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Peptide

<400> SEQUENCE: 9

Asp Leu Thr Phe Gly Trp His Ala Thr Lys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Peptide

<400> SEQUENCE: 10

Asp Leu Thr Phe Gly Trp His Ala Lys
1               5

<210> SEQ ID NO 11
<211> LENGTH: 9
<212> TYPE: PRT
<213> ORGANISM: Artificial Sequence
<220> FEATURE:
<223> OTHER INFORMATION: Peptide

<400> SEQUENCE: 11

Asp Leu Thr Phe Gly Trp His Tyr Lys
1               5
```

CYCLIC PEPTIDE AND IMAGING COMPOUND COMPOSITIONS AND USES FOR TARGETED IMAGING AND THERAPY

RELATED APPLICATION

This application claims priority to U.S. Provisional Patent Application Ser. No. 60/495,658, filed Aug. 15, 2004, and entitled "Cyclic Peptides and Uses for Targeted Imaging and Therapy of Solid Tumors."

STATEMENT OF GOVERNMENT INTEREST

The present invention was made in whole or in part using funds from NIH/NCI Grant Number U54 CA90810, ATP/THECB Grant Number 003657-0042-2001, and NIH/NIBIB Grant Number EB000174. The U.S. Government has certain rights in the invention.

FIELD OF THE INVENTION

The present invention relates to cyclic peptide compositions that may be used in targeted imaging and therapy of solid tumors. It also includes imaging agents. The present invention also relates to methods of making and using such cyclic peptide compositions and imaging agents.

BACKGROUND

Targeted drug or diagnostic compound delivery offers many beneficial effects, including increased drug efficacy, lesser side effects, and better diagnostic capabilities. Numerous compounds have been developed to target specific marker molecules, but additional or more versatile and effective targeting compounds are always needed.

Numerous studies have shown that the formation of new vasculature (angiogenesis) is required for progression of malignant tumors and secondary lesion formation as a result of metastasis. Angiogenesis depends on vascular endothelial cell proliferation, migration, and invasion. A family of adhesion molecule receptors known as integrin receptors regulates these processes. Among the various members of the integrin family, $\alpha_v\beta_3$ plays a very significant role in angiogenesis. Integrin $\alpha_v\beta_3$ is minimally expressed on resting or normal blood vessels, but its expression is significantly up-regulated on vascular cells within human tumors. Angiogenesis can be inhibited by anti-$\alpha_v\beta_3$ antibody. Additionally, antagonists of $\alpha_v\beta_3$ may significantly inhibit angiogenesis induced by cytokines and solid tumor fragments. Clinical trials of a monoclonal antibody against $\alpha_v\beta_3$ (Vitaxin™, MedImmune, Inc., Gaithersburg, Md.) showed that the treatment appeared safe and potentially active. However, heterogeneous responses were observed even within the same patient (i.e. some metastases remained stable while others progressed).

For clinical trials relating to $\alpha_v\beta_3$, a surrogate marker or noninvasive imaging technique that could assess different receptor levels and different activities among different metastases would be extremely helpful in evaluating early treatment responses and understanding the mechanisms behind different responses. It has been demonstrated that MRI imaging of solid tumor angiogenesis may be accomplished using a liposomal paramagnetic imaging agent targeted to endothelial $\alpha_v\beta_3$ via the anti-$\alpha_v\beta_3$ monoclonal antibody LM609.

Others have used radiolabeled RGD-containing peptide, which binds to $\alpha_v\beta_3$, to image tumor cells expressing $\alpha_v\beta_3$. For example, $^{125}$I-labeled 3-iodo-tyr-cyclo(Arg-Gly-Asp-tyr-Val) exhibits high affinity and selectivity for the $\alpha_v\beta_3$ integrin. Additionally, $^{18}$F-labeled RGD-containing glycopeptide has been used for noninvasive PET imaging of $\alpha_v\beta_3$ expression. Specifically, a cyclic pentapeptide, cyclo(Lys-Arg-Gly-Asp-phe) ("c(KRGDf; SEQ ID NO. 3)" or "cyclic RGD peptide") was used. The D-Phe construction in this molecule produces a characteristic βII'-turn at the RGD site in a kinked conformation responsible for the $\alpha_v\beta_3$ integrin binding selectivity. Furthermore, the Lys group may be derivatized at the β-NH$_2$ position without changing the spatial structure of the peptide and thus the binding affinity to the $\alpha_v\beta_3$ integrin. Further PET studies using $^{18}$F-labeled RGD peptides have demonstrated high and specific uptake of the radiotracer in human tumor xenograft.

Matrix metalloproteinases (MMPs) are a family of enzymes capable of degrading the constituents of the extracellular matrix and the basement membrane. There is growing evidence that the MMPs are important not only in tumor invasion and metastases, but also in the creation and maintenance of a microenvironment that facilitates growth and angiogenesis of tumors at primary and metastatic sites. MMPs are up-regulated in virtually all human and animal tumors as well as in most tumor cell lines. Recent studies indicate that expression of MMPs is in general more common in nearby stromal cells than in tumor cells. Many MMPs are induced in connective tissue cells, including fibroblasts and inflammatory cells, as a response to a tumor. These results suggest that MMPs are important contributors to tumor progression and provide the rationale for developing new cancer drugs and diagnostic agents that target MMP activity.

There are reports that suggest that expression of MMPs may have diagnostic or prognostic value. For example, a small study has suggested that serum gelatinase A (an MMP) levels were higher in men with prostate cancer than in men with benign prostatic hypertrophy or normal prostates. In colon cancer samples, immunohistochemical detection of interstitial collagenase (another MMP) is associated with a poor prognosis independent of Duke's stage. These observations are significant because they not only link MMPs with aggressive malignant progression, but they also suggest that tumor-related expression of MMPs may provide important prognostic information that could help direct therapeutic recommendations, including the possibility of targeting inhibition of one or more MMPs.

Additionally, the ability to non-invasively image MMP expression, if properly developed, may be helpful in monitoring treatment responses to MMP inhibitors. Many small molecules containing both hydroxamate and non-hydroxamate zinc binding sites, as well as natural products such as tetracyclines and their derivatives, were developed as MMP inhibitors. Several MMP inhibitors have been tested for clinical trials in cancer patients. However, marimastat and batimastat, two promising MMP inhibitors, have been disappointing in a Phase III clinical trial. Clinical studies with MMP inhibitors have lacked endpoint assessment of MMP-inhibitory activity and the relationship between target modulation and clinical response. This, coupled with disappointing results obtained with MMP inhibitors, suggests that standard clinical trial endpoints are insufficient for the evaluation of molecularly targeted cytostatic agents. Accordingly, there is a great need for the ability to analyze drug efficacy through surrogate markers for MMP expression and/or MMP activity using non-invasive imaging techniques.

It has been suggested that the effect of MMP inhibitors may be stage-specific and tumor-specific. Recent studies support a role for MMPs in earlier stages of the tumor progression continuum. For example, batimastat treatment decreases the number of intestinal adenomas and pancreatic islet cell tumors in the min and RIP-Tag mouse models, respectively; however, tumor burden is diminished in RIP-Tag mice only if the drug is administered before the emergence of large invasive carcinomas. When batimastat is given at advanced tumor stages, no efficacy is observed. These studies establish a spatial and temporal significance for MMPs during tumorigenesis. An analysis of the expression patterns of MMPs in the cancer type and stage and its correlation with treatment outcome may allow a more rational decision on the selection of specific MMP inhibitors and optimal treatment schedule. Additionally, given the importance of MMPs early in tumor development, imaging compounds focused on MMPs are needed.

Using phage display technology, Pasqualini and colleagues have identified a cyclic decapeptide, c(CTTHWG-FTLC; SEQ ID NO. 1) (FIG. 1), which not only exhibits selective and potent inhibition of MMP-2 (gelatinase A) and MMP-9 (gelatinase B), but also homes to tumor vasculature in vivo. However, this peptide is very unstable. It degrades completely in cell culture medium in three hours (FIG. 2), preventing its practical use in vivo. This instability is likely due to the use of a disulfide bond to cyclize the polypeptide. More stable peptides are needed for MMP targeting.

SUMMARY OF THE INVENTION

The present invention relates to targeting cyclic peptides, imaging agents, and compositions containing one or more of the cyclic peptides or imaging agents.

One embodiment of the present invention relates to at least one stable cyclic polypeptide of the formula $c(X_1X_2X_3HWGFTLX_4;$ SEQ ID NO. 4), wherein $X_1$, $X_2$, $X_3$ and $X_4$ may each be an L-amino acid, a D-amino acid, or a non-natural amino acid and one or more of amino acids $X_1$, $X_2$, $X_3$ and $X_4$ may be omitted (hereinafter, collectively, the "HWGFTL (SEQ ID NO. 5) peptides").

In certain embodiments, the peptides may be cyclized through an amide bond. They may be include a head-to-tail linkage, a side chain-to-tail linkage, or a side chain-to-side chain linkage.

In a specific embodiment, one of amino acids $X_1$, $X_2$, $X_3$, or $X_4$ is tyrosine. In other specific embodiments, the HWGFTL (SEQ ID NO. 5) peptides may include c(ATAHWGFTLβA; SEQ ID NO. 6), c(ATTHWGFTLD; SEQ ID NO. 7), c(KTTHWGFTLD; SEQ ID NO. 8), c(KTAHWGFTLD)NH$_2$; (SEQ ID NO. 9), c(KYHWG-FTLD)NH$_2$ (SEQ ID NO. 11), c(KAHWGFTLD)NH$_2$ (SEQ ID NO. 10), c(KAHWGFTLD; SEQ ID NO. 10), and combinations thereof.

In another embodiment, the HWGFTL (SEQ ID NO. 5) peptides may be conjugated to an imaging agent, such as an imaging agent useful in medical diagnostics. Imaging agents may include NIR imaging agents, MRI imaging agents, and nuclear imaging agents.

NIR imaging agents may include a near infrared dye, such as a cyanine or indocyanine derivative. Such dyes used in specific embodiments of the invention include Cy5.5, IRDye800, indocyanine green (ICG), indocyanine green derivatives and combinations thereof. In one specific embodiment, the dye includes a tetrasulfonic acid substituted indocyanine green (TS-ICG). Particularly useful TS-ICGs include TS-ICG carboxylic acid or TS-ICG dicarboxylic acid.

In embodiments in which the HWGFTL (SEQ ID NO. 5) peptide contains tyrosine, the tyrosine may be labeled with $^{131}$I, $^{125}$I, or $^{124}$I.

In embodiments containing an MRI imaging agent, the MRI imaging agent may include Gd, Mn or iron oxide.

In embodiments containing a nuclear imaging agent, the agent may be a radionuclide, such as $^{18}$F, $^{131}$I, $^{124}$I, $^{125}$I, $^{111}$In, $^{99m}$Tc, $^{67}$Cu, $^{64}$Cu, $^{68}$Ga and combinations thereof. In particular the imaging agent may be a PET imaging agent.

In various embodiments, the cyclic HWGFTL (SEQ ID NO. 5) peptides may be directly covalently bound or indirectly covalently bound to at least one imaging agent. At least one linker molecule may be included in the composition. Suitable linkers include poly(L-Glutamic Acid), polyethylene glycol, an aliphatic chain, Lysine, a dual functional amino acid and combinations thereof.

In some embodiments, at least one additional imaging agent functional in an additional imaging modality may be included in the composition.

In selected embodiments, the HWGFTL (SEQ ID NO. 5)-containing cyclic peptide imaging agent composition may be useful in detecting MMP in an animal, such as a human. Specifically, the cyclic peptide may be useful in targeting the composition to MMP molecules. In particular embodiments, the animal may have or be suspected of having cancer, osteoarthritis, intra-amniotic infection, respiratory disease having tissue destruction, bacterial meningitis, periodontal disease, rheumatoid arthritis, heart disease such as atherosclerosis and combinations thereof.

The HWGFTL (SEQ ID NO. 5)-containing cyclic peptides of the present invention may additionally be conjugated to therapeutic agents, which they may target to areas expressing MMPs. In specific embodiments, the therapeutic agent may include a chemotherapeutic agent, such as camptothecin, paclitaxel, doxorubicin, methotrexate and combinations thereof. It may also include a radionuclide, such as $^{131}$I or $^{90}$Y, or combinations thereof. These therapeutic compositions may include a linker, as described above with respect to imaging compositions. Further, in some embodiments of the invention, a single cyclic peptide composition may include both an imaging agent and a therapeutic agent, or even more than one type of each. Embodiments containing therapeutic agents may be used to treat MMP-related diseases, such as cancer, osteoarthritis, intra-amniotic infection, respiratory disease having tissue destruction, bacterial meningitis, periodontal disease, rheumatoid arthritis, heart disease such as atherosclerosis and combinations thereof.

Finally, in specific embodiments of both therapeutic agent and imaging agent-containing compositions described above, more than one copy of the cyclic peptide may be present in the same covalently bound composition.

In other embodiments of the present invention, a cyclic RGD peptide may be conjugated to an NIR imaging agent to form another cyclic peptide imaging agent composition. In this composition, the NIR agent may be similar to that described above with respect to HWGFTL (SEQ ID NO. 5) peptide compositions. Other imaging agents and/or therapeutic agents may be present in the composition, as may linkers, all also in the manner described above with respect to HWGFTL (SEQ ID NO. 5) peptide compositions. Finally, multiple copies of the cyclic RGD peptide may be present in the same covalently bound composition.

All cyclic peptide compositions of the present invention may be formed by cyclizing a short peptide, then adding the relevant linker, imaging agent, and/or therapeutic agent.

In specific embodiments of the invention, the composition includes an NIR imaging agent and may be used to obtain an NIR image of a solid tumor in an animal, such as a human. The solid tumor may be approximately less than 5 cm in diameter, less than 1 cm in diameter, less than 5 mm in diameter, or less than 2 mm in diameter, depending in part on its location, type, stage, and the imaging agent used. The tumor may, for example be a melanoma or a breast cancer. The tumor may be located in a sentinel lymph node. The image of the tumor may be obtained in a variety of manners, such as non-invasively, intraoperatively, through endoscopy, and through laproscopy.

Additionally, different cyclic peptides coupled with different imaging agents, either functional in different modalities or distinguishable in the same modality, may be used to obtain images showing different tumor regions. For example, one NIR imaging agent may be coupled to an RGD peptide while another, distinguishable NIR agent maybe coupled to an HWGFTL (SEQ ID NO. 5) peptide, thereby allowing one to obtain two images of the same tumor showing the located of two different target molecules. Such images are often most useful if rendered as a dual or multiple-color single image.

All imaging compositions and techniques described above may be used to determine the efficacy of treatment, or to help in selecting an appropriate treatment for a given tumor. Compositions containing both treatment and imaging agents may be used, for example, to determine if a treatment is reaching a target site.

Yet another embodiment of the invention relates to an imaging agent composition including TS-ICG or its derivatives, including carboxylic acid and dicarboxylic acid forms. These molecules may be made by substituting at least one sulfonic acid group on an ICG molecule. In specific embodiments, at least four sulfonic acid groups are substituted. To form carboxylic acid forms, at least one carboxylic acid groups may be substituted.

For a more complete understanding of the present invention and the advantages thereof, reference is now made to the following drawings and description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A and 4B show a representative in vivo bright light image (FIG. 4A) and a representative in vivo NIR image (FIG. 4B) of subcutaneously implanted KS1767 tumors. Cy5.5-c(KRGDf; SEQ ID NO. 3) was injected intravenously at a dose of 6 nmol/mouse. Images were acquired 24 hours after imaging agent injection. Arrows indicate tumors.

FIGS. 6A and 6B show representative in vivo NIR images of subcutaneous KS1767 tumors. To obtain the images, Cy5.5-c(KRGDf; SEQ ID NO. 3) was injected intravenously at a dose of 6 nmol/mouse without pre-injection of c(KRGDf; SEQ ID NO. 3) (FIG. 6A) or at 1 hour after intravenous injection of c(KRGDf; SEQ ID NO. 3) at a dose of 600 mmol (FIG. 6B). Images were acquired 24 hours after imaging agent injection. Tumors are indicated by arrows.

FIG. 12 shows the results of in vitro assays with Cy5.5-c(KYHWGFTLD)NH$_2$ (SEQ ID NO. 11) binding to PC-3 cells and U87 cells. Cells were incubated with Cy5.5-c(KYHWGFTLD)NH$_2$ (SEQ ID NO. 11) (10 μM) at 37° C. for 10 minutes, then stained with Sytox Green for nuclei (green color). Red indicates the imaging agent.

Cy5.5-c(KAHWGFTLD)NH$_2$ (SEQ ID NO. 10) was injected intravenously at a dose of 15 nmol per mouse. Arrows indicate tumors.

Figure 14:
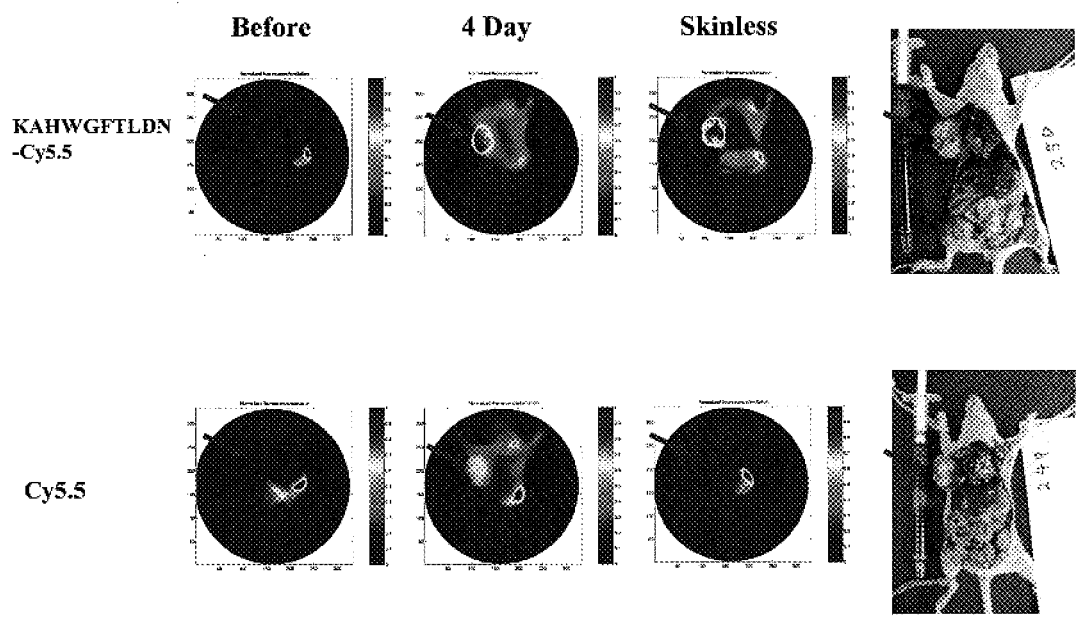

FIG. 14 shows representative in vivo NIR images of subcutaneous SKBr-3 tumors. Cy5.5-c(KAHWGFTLD) NH$_2$ (SEQ ID NO. 10) or Cy5.5 alone was injected intravenously at a dose of 15 nmol per mouse. Arrows indicate tumors.

Figure 15:
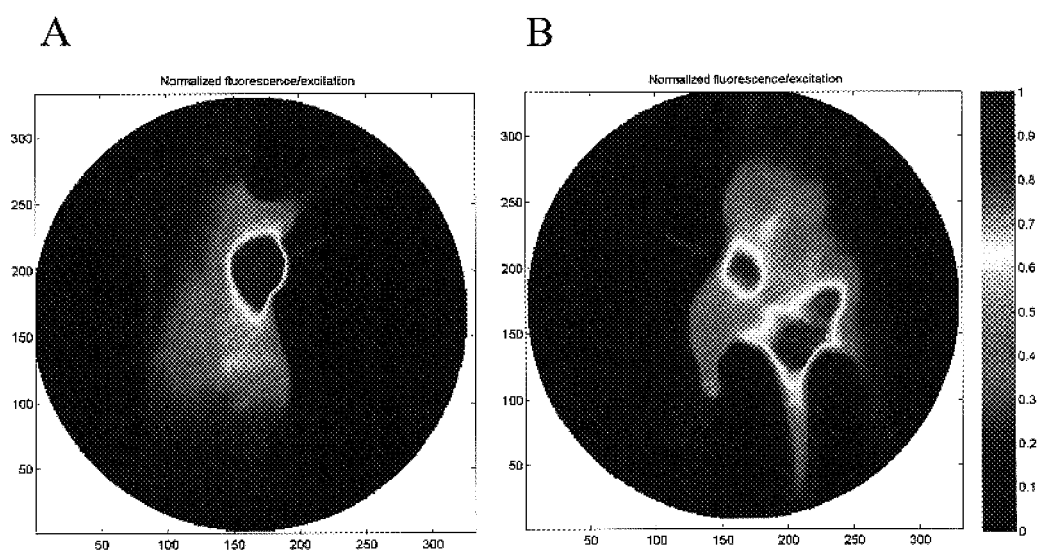

FIGS. 15A and 15B show a representative in vivo NIR fluorescent image of subcutaneous MDA-MB-468 tumors (FIG. 15A) and KS1767 tumors (FIG. 15B) with Cy5.5-c(KAHWGFTLD)NH$_2$ (SEQ ID NO. 10) (15 nmol per mouse). Arrows indicate tumors.

FIGS. 16A-E show bright light (FIGS. 16A and 16C) and NIR fluorescence imaging (FIGS. 16B and 16D) of a mouse bearing orthotopic human U87 glioma cells. Imaging was performed in the intact animal (FIGS. 16A and 16B) and in the excised brain tissue (FIGS. 16C and 16D) 12 days after intracranial injection of 1×10$^6$ tumor cells and 38 hours after imaging agent injection. The brain tissue was stained with H&E (Hematoxylin and Eosin stain; a common pathology stain) to show the location of the tumor (indicated by arrows in FIG. 16E). Cy5.5-c(KAHWGFTLD)NH$_2$ (SEQ ID NO. 10) was injected intravenously at a dose of 15 nmol/mouse. Arrows indicate tumors. The bar located to the right of FIG. 16E indicates 1 cm in actual length.

Figure 17:
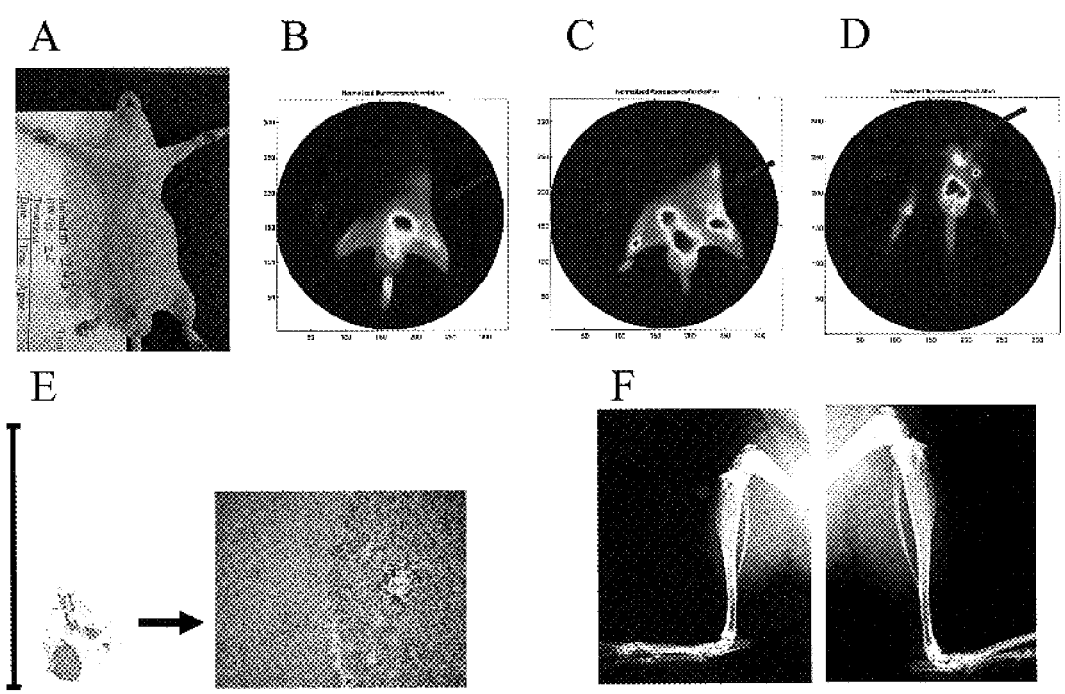

FIGS. 17A-F show NIR imaging of subcutaneous U87 tumors and intratibia PC-3 tumors (indicated by arrows) three days after tumor inoculation. Images were acquired at 5 minutes (FIG. 17B), 1 day (FIG. 17C), and 2 days (FIG. 17D, in skinless mouse) after intravenous injection of Cy5.5-c(KAHWGFTLD)NH$_2$ (SEQ ID NO. 10). The tumors were not visible in bright light images (FIG. 17A). U87 produced a small lesion less than 2 mm in diameter (FIG. 17E, bar indicates 1 cm in actual length, stained with H&E). X-ray could detect no bone lesion in the legs of the mouse injected with PC-3 cells (FIG. 17F).

FIG. 18 shows a comparison of NIR imaging obtained with Cy5.5-c(KAHWGFTLD)NH$_2$ (SEQ ID NO. 10) and with a Cy5.5-scrambled peptide imaging agent, Cy5.5-c(KHGLTWFAD)NH$_2$ (SEQ ID NO. 12) in mice inoculated with PC-3 human prostate tumors 3 days earlier. PC-3 cells were injected intratibially in the left legs (indicated by arrows). Saline was injected into the tibia region of contralateral legs as a control (indicated by arrow head). Images were acquired 24 hours after contrast injection.

Figure 19:
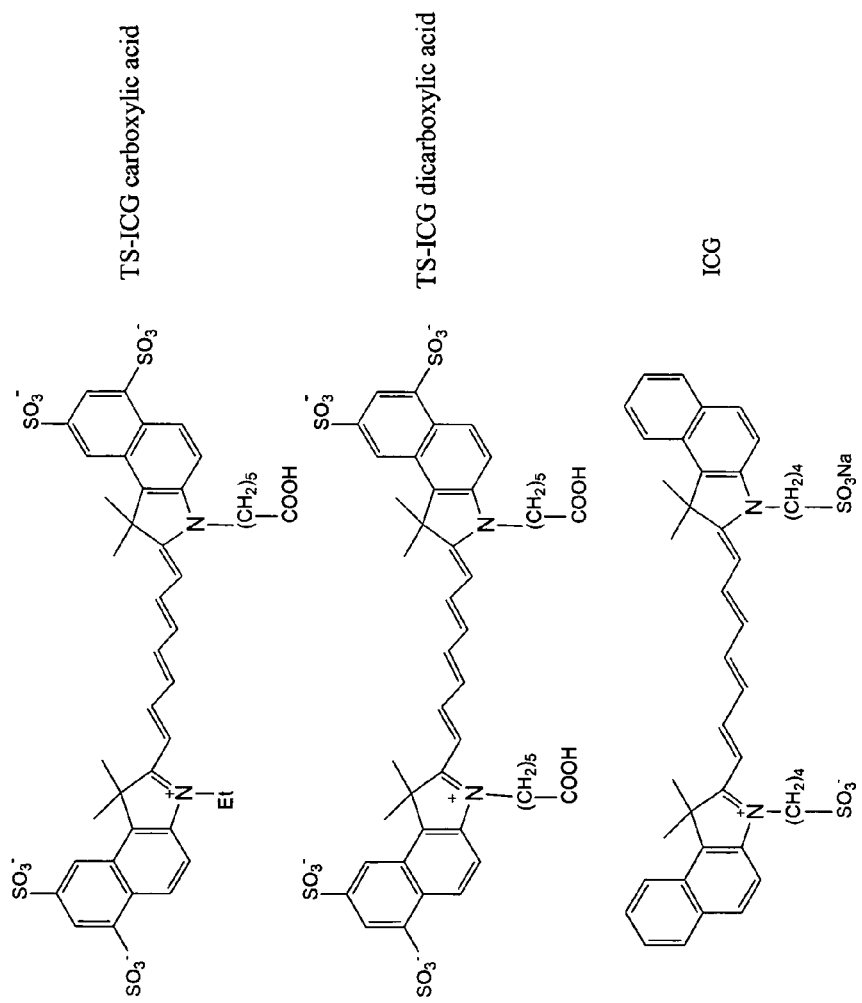

FIG. 19 shows structures of Mono- and Di-functional ICG derivatives.

Figure 20:
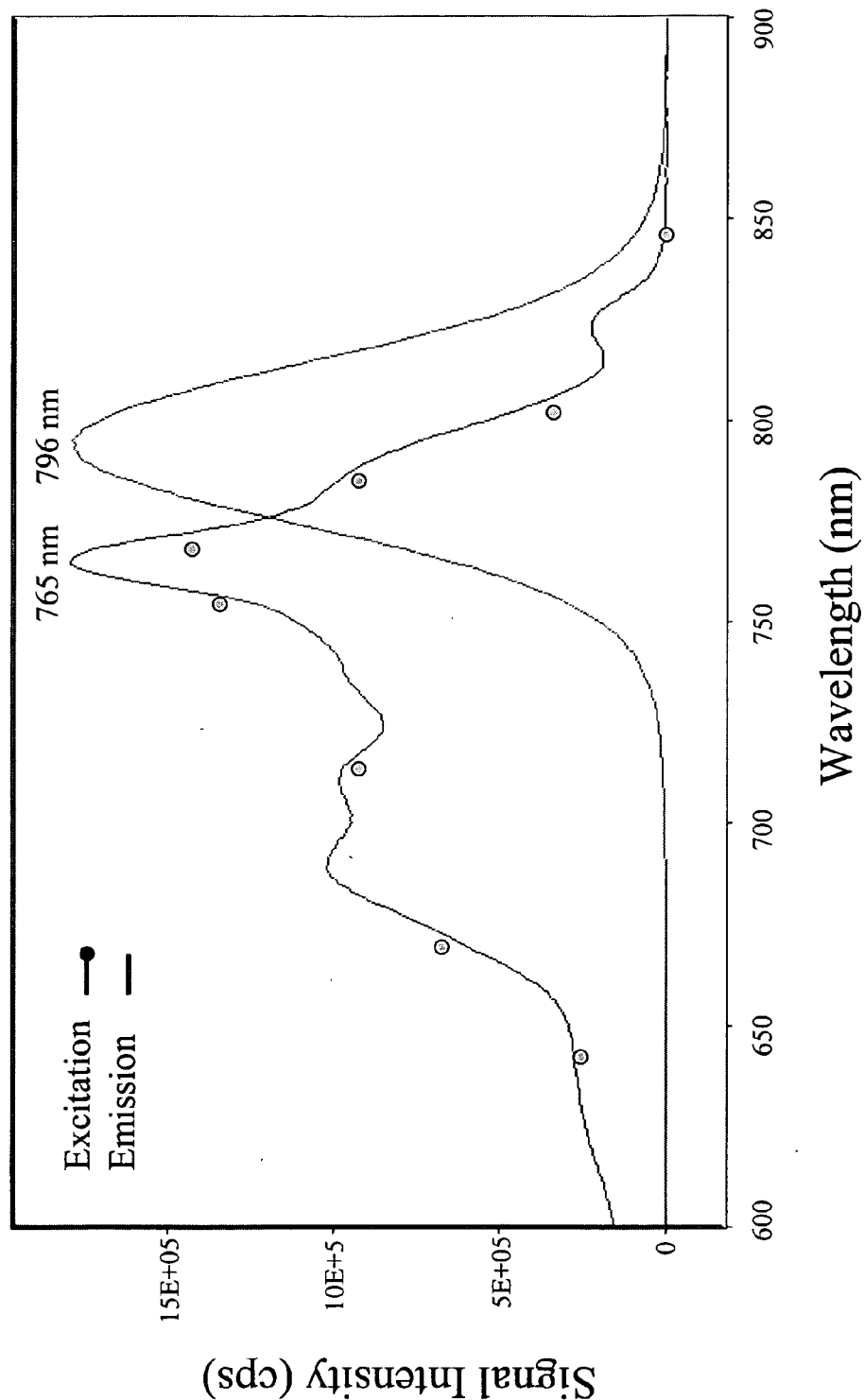

FIG. 20 shows the fluorescence spectra of TS-ICG carboxylic acid.

Figure 21:
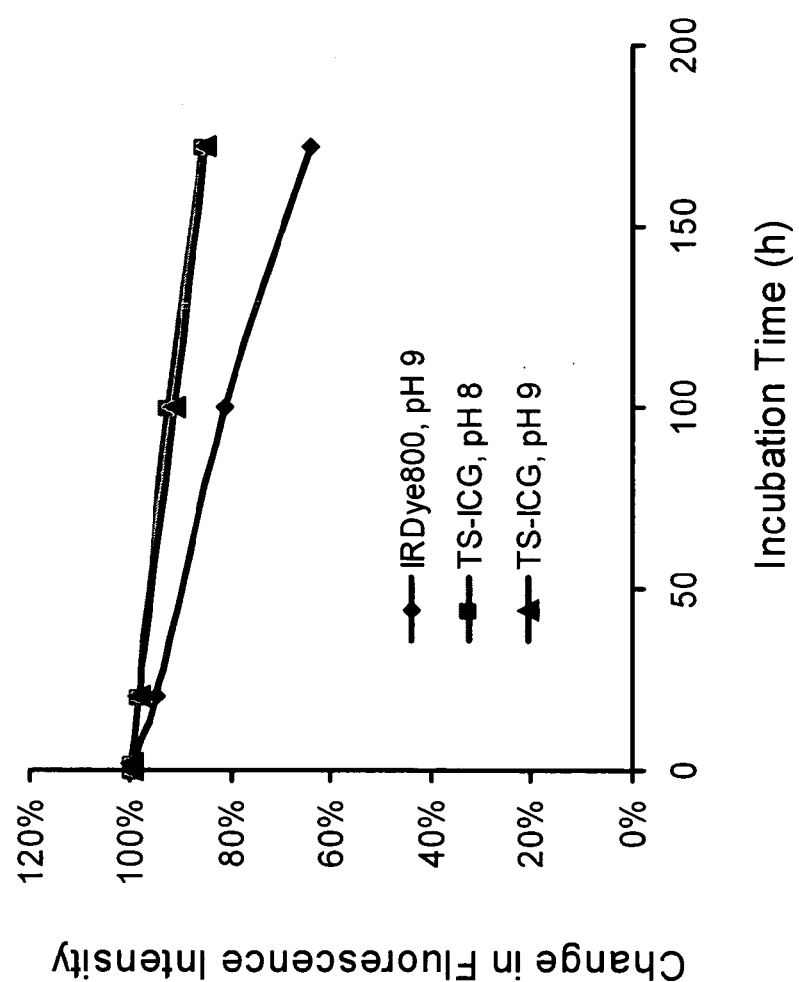

FIG. 21 shows the stability of TS-ICG carboxylic acid in basic conditions (pH 8-9) compared with IRDye800.

Figure 22:
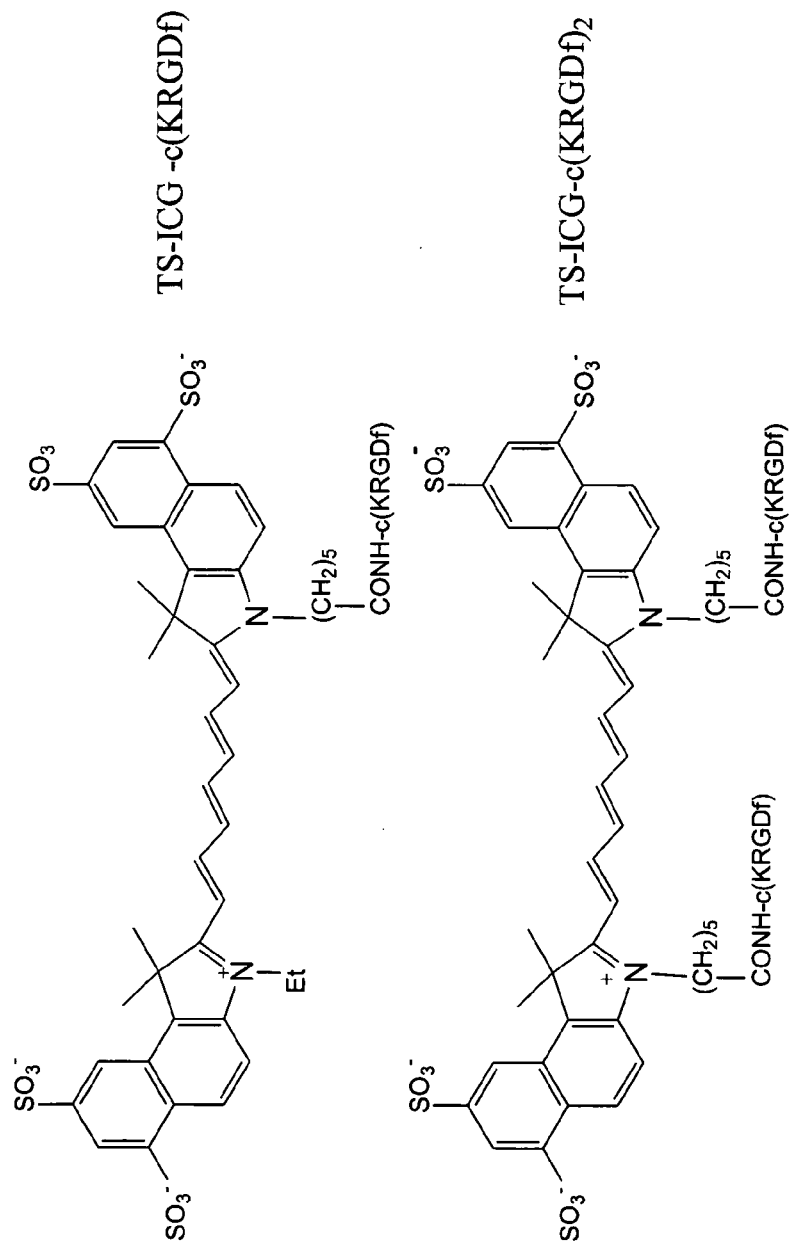

FIG. 22 shows example monomeric and dimeric structures of RGD imaging agents with TS-ICG dyes. The dimeric imaging agent contains two c(KRGDf; SEQ ID NO. 3) peptides.

FIG. 23 shows a comparison in NIR imaging using monomeric and dimeric RGD imaging agents.

Figure 24:
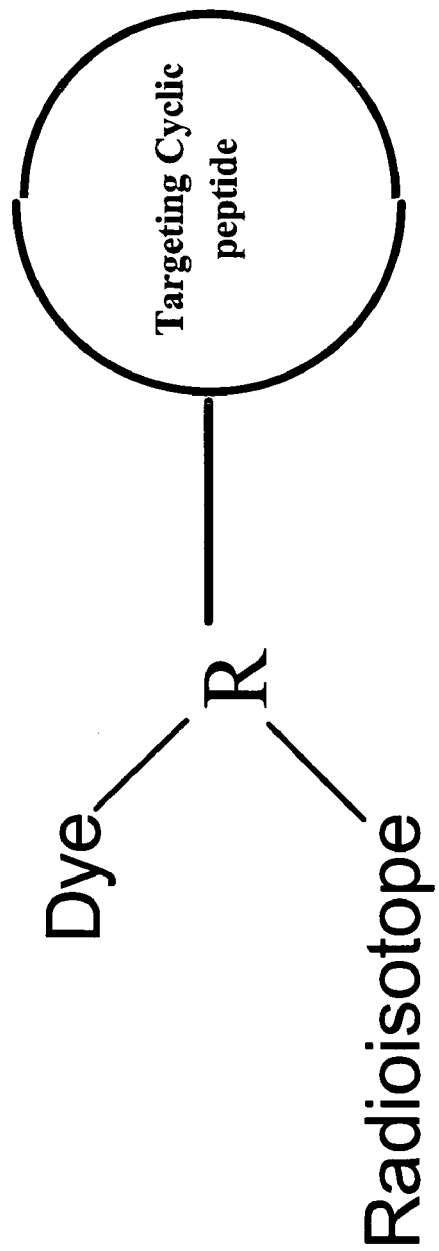

FIG. 24 is an example structure of a composition for dual modality imaging.

Figure 25:
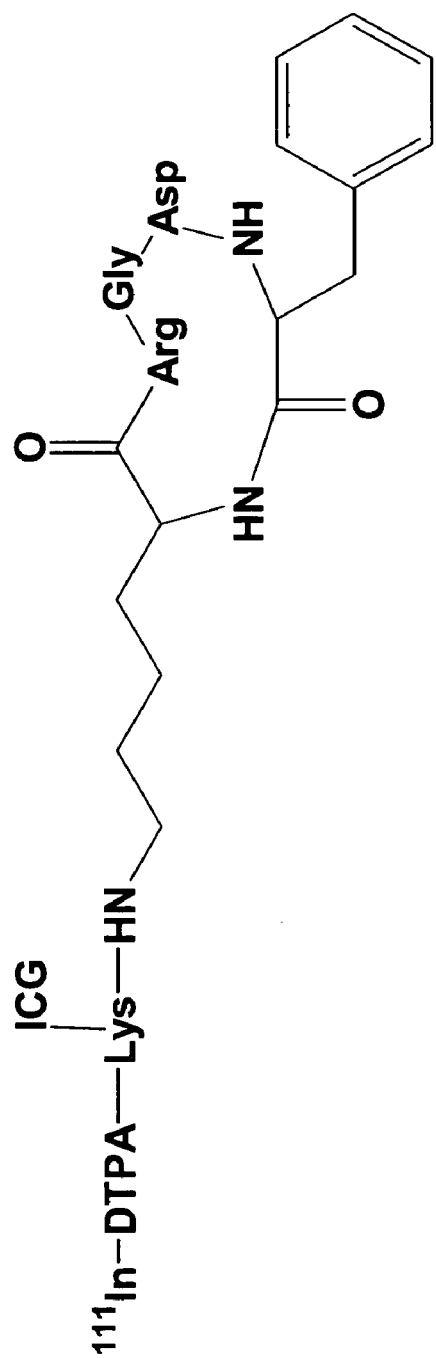

FIG. 25 is a dual modality imaging agent, $^{111}$In-DTPA-K(ICG)-c(KRGDf; SEQ ID NO. 3), where ICG may be TS-ICG or IRDye800.

Figures 26A, 26B:
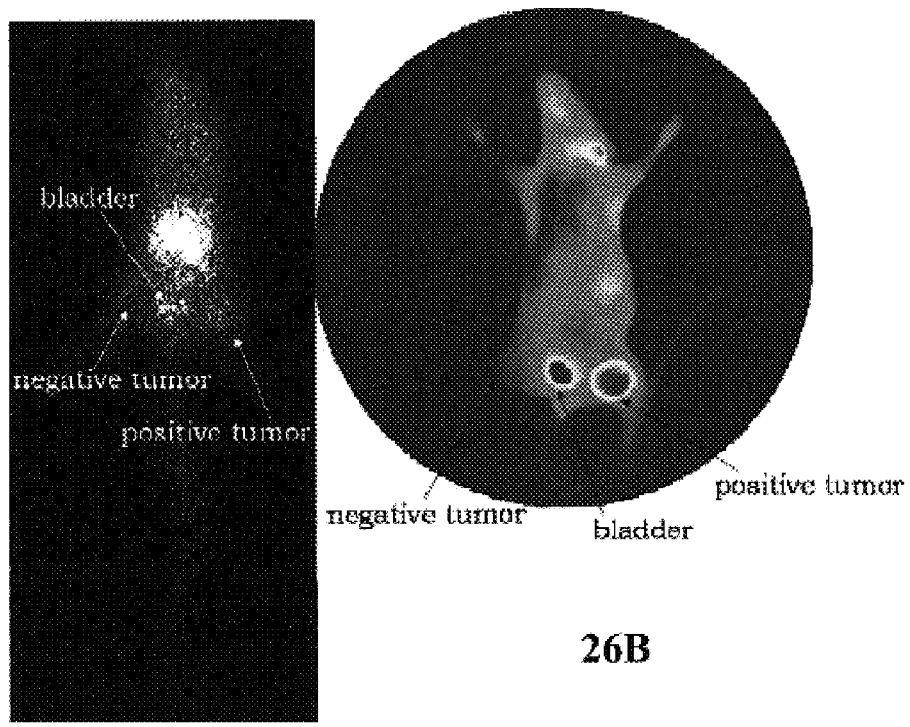

FIGS. 26A and 26B show both nuclear and optical images of a mouse that was injected with the dual modality labeled imaging agent $^{111}$In-DTPA-K(ICG)-c(KRGDf; SEQ ID NO. 3), where ICG=IRDye800. FIG. 26A shows a nuclear gamma image of the mouse obtained using nuclear imaging. FIG. 26B shows a NIR optical image of the same mouse.

Figure 27:
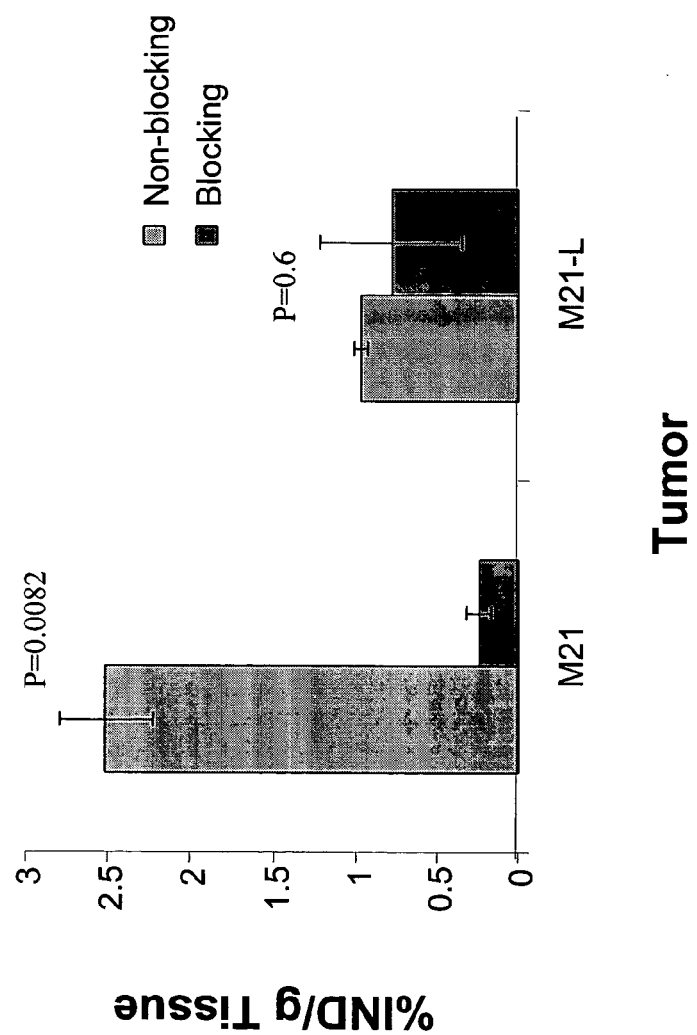

FIG. 27 shows a cut and count analysis of melanoma tumors in mice injected with $^{111}$In-DTPA-K(ICG)-c(KRGDf; SEQ ID NO. 3), where ICG=IRDye800.

Figure 28:
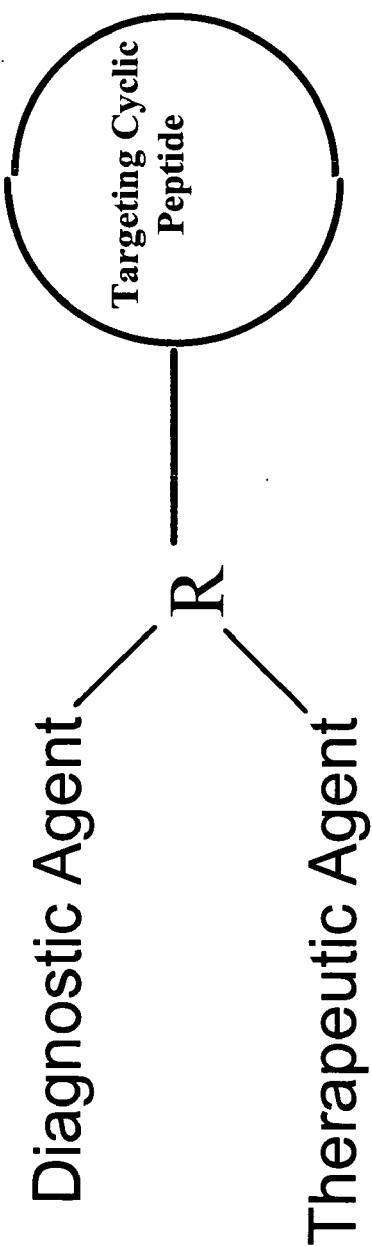

FIG. 28 is a composition for both therapy and monitoring of drug localization.

Figure 29:
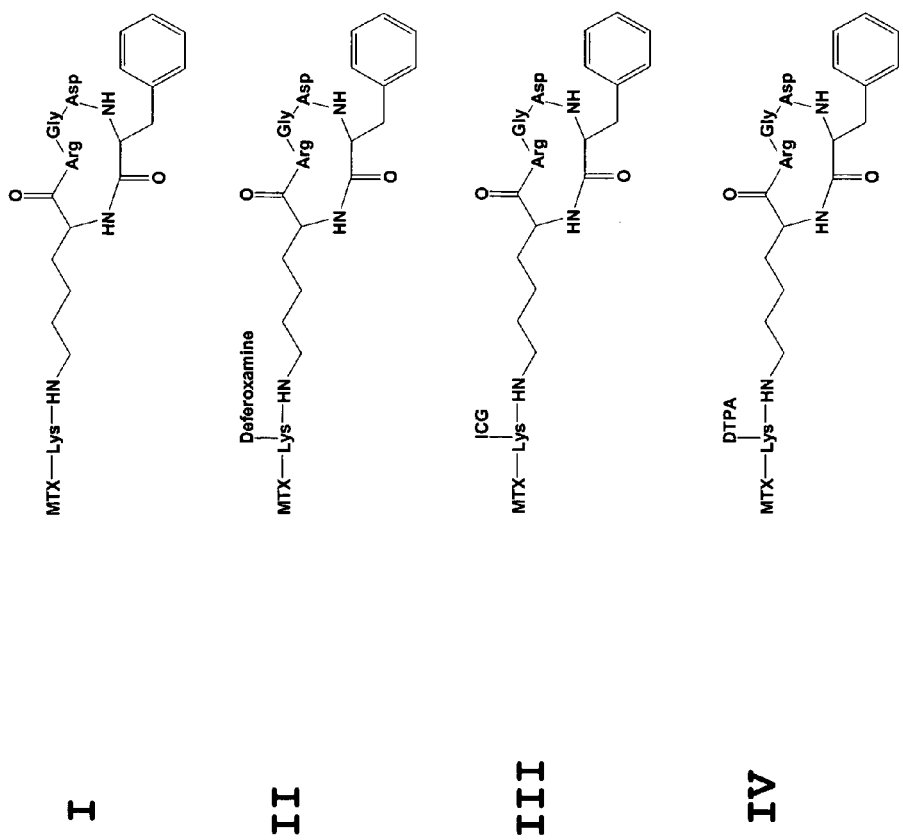

FIG. 29 shows an example therapeutic compound (I) and three example embodiments of combined imaging and therapeutic compounds (II-IV).

Figure 30:
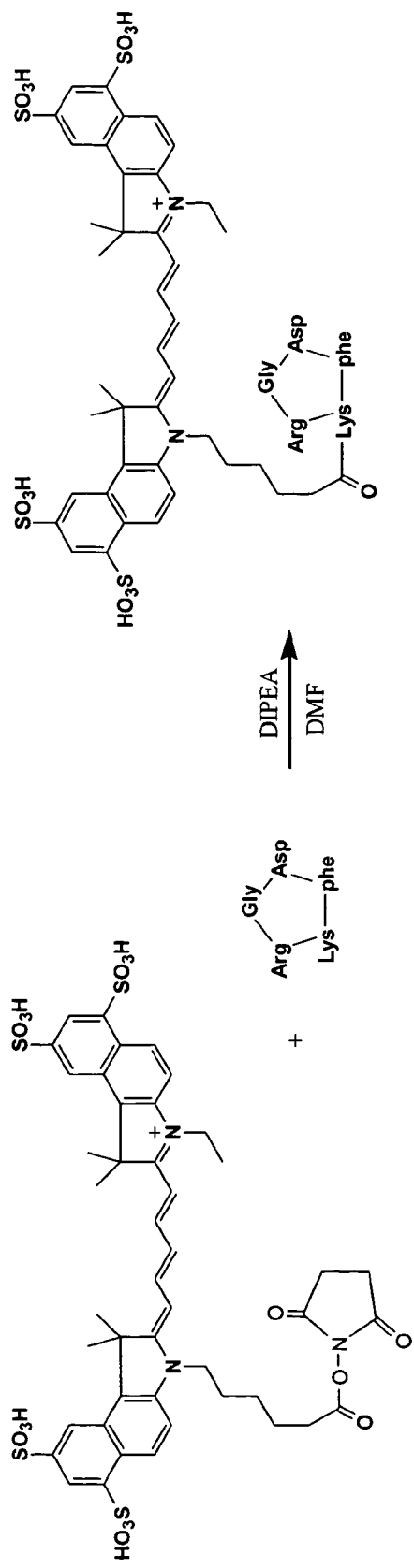

FIG. 30 shows a synthesis method for a Cy5.5-c(KRGDf; SEQ ID NO. 3) imaging agent.

Figure 31:
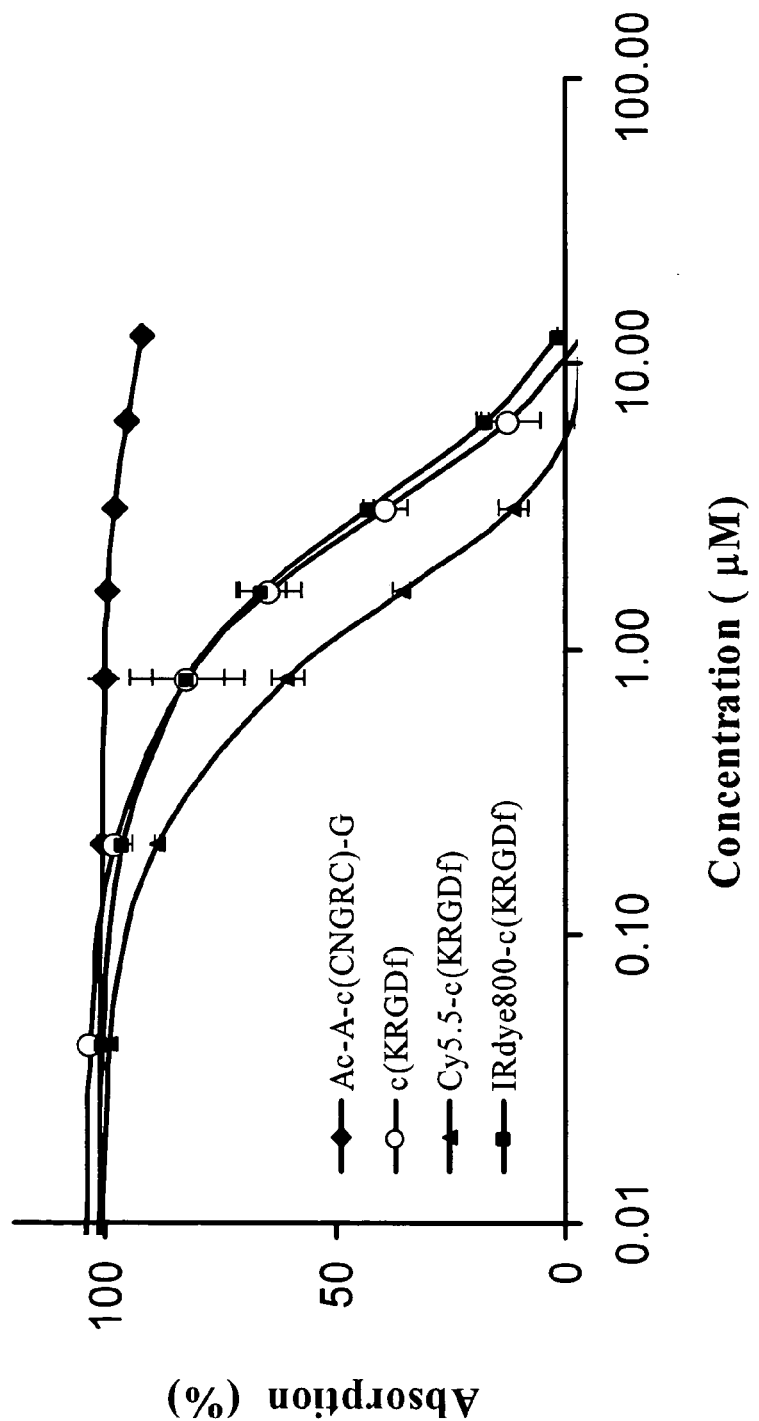

FIG. 31 shows the dose-dependent inhibition of adhesion of KS1767 cells to vitronectin-coated microplate wells by c(KRGDf; SEQ ID NO. 3) and NIR dye imaging agents containing the cyclic peptide.

Figure 32:
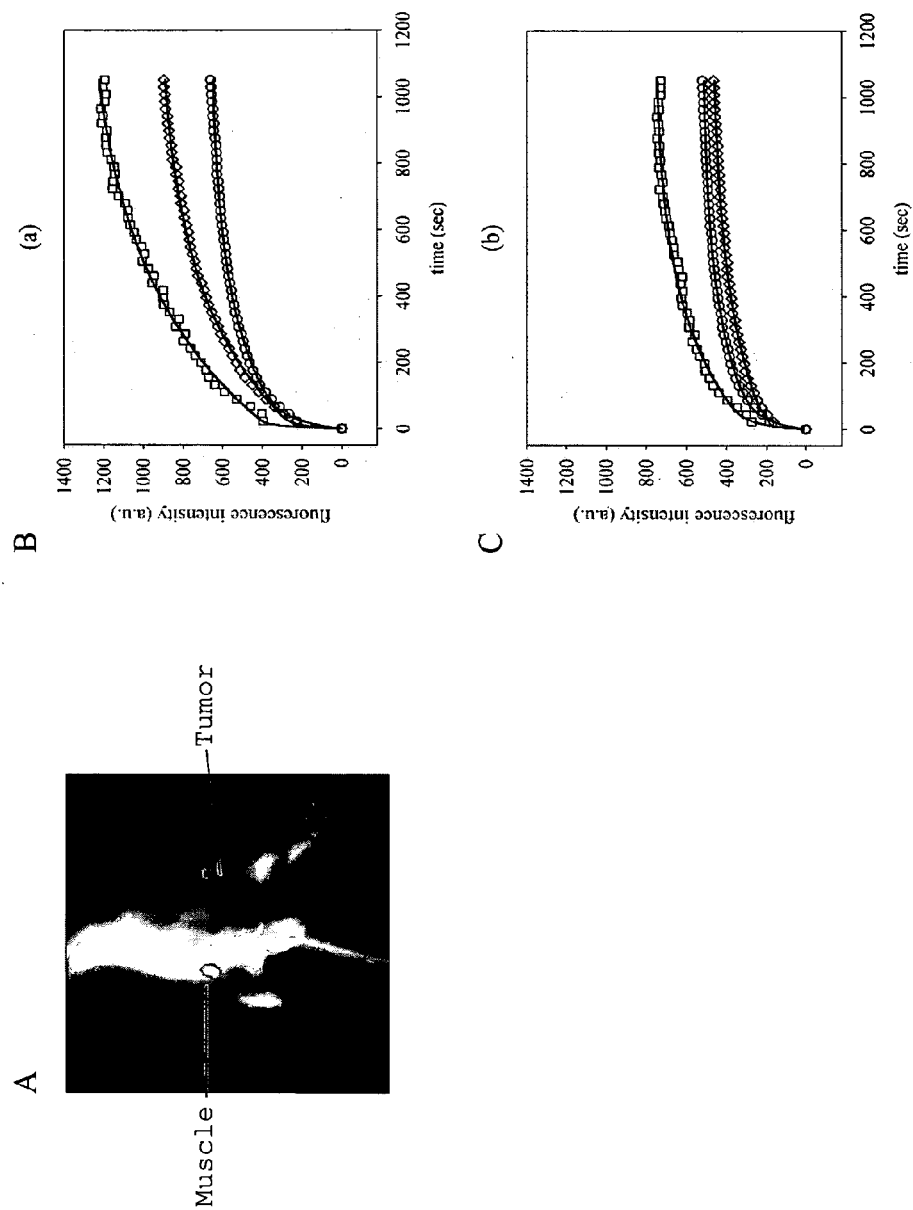

FIGS. 32A-C show a comparison in the fluorescence intensity versus time profiles between a tumor region of interest (ROI) and a normal muscle ROI areas. FIG. 32A shows a bright light image of the ROIs. FIG. 32B shows data acquired from the tumor ROI and FIG. 32C shows data acquired from the normal muscle ROI.

Figure 33:
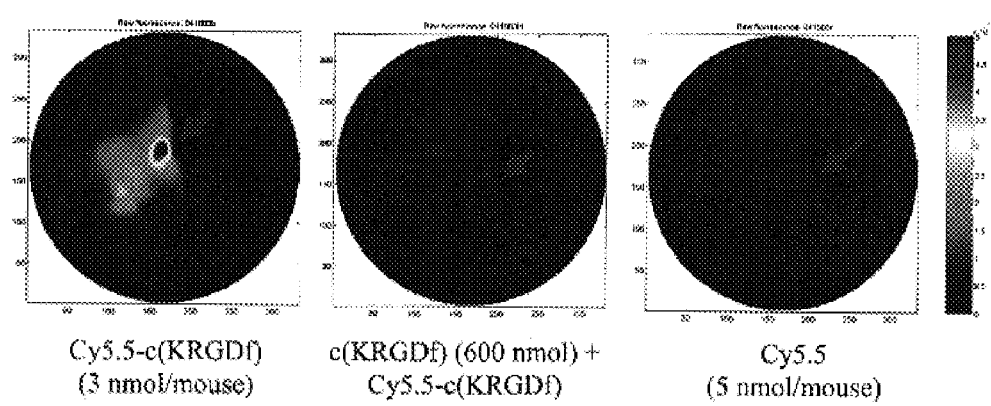

FIG. 33 shows representative in vivo NIR fluorescent images of subcutaneously implanted KS1767 tumors (n=2). Images were acquired 24 hours (hr) after i.v. injection of Cy5.5-c(KRGDf; SEQ ID NO. 3) (6 nmol/mouse) (left), c(KRGDf; SEQ ID NO. 3) (600 nmol/mouse) plus Cy5.5-c(KRGDf; SEQ ID NO. 3) with 1 hr interval (middle), or Cy5.5 (6 nmol/mouse) (right).

Figure 34:
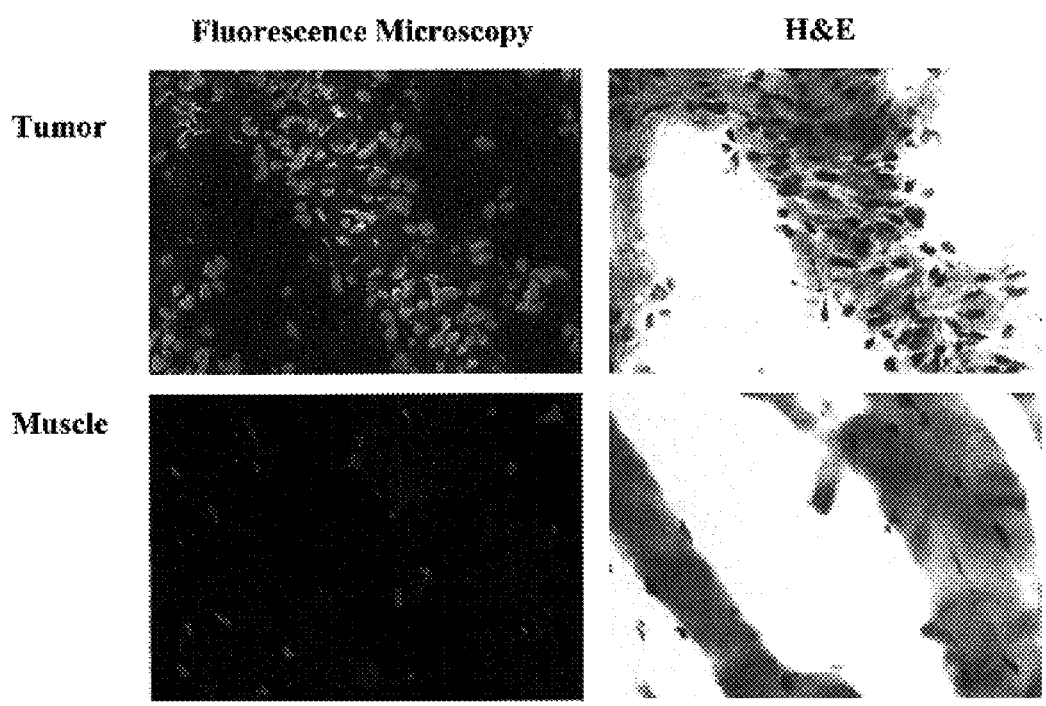

FIG. 34 shows ex vivo analysis of Cy5.5-c(KRGDf; SEQ ID NO. 3) distribution in a KS1767 tumor excised 48 hr after its intravenous injection. Fluorescence microscopic images were obtained from sectioned tissues (6 µm thick). The same slide was also stained with H&E. Red: Cy5.5-c(KRGDf; SEQ ID NO. 3); Green: nuclei was stained with Sytox Green. Original object magnification was ×10.

Figure 35:
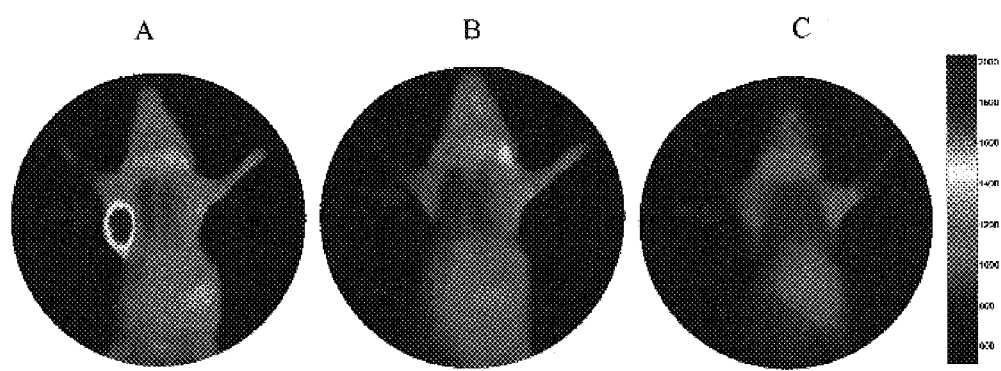

FIG. 35 shows representative fluorescence images obtained 24 hr after intravenous injection of IRDye800-c(KRGDf; SEQ ID NO. 3) (3 nmol/mouse) in A: mice bearing integrin-positive M21 melanoma, and B: integrin-negative M21-L melanoma (n=2). A representative image of mouse injected with only IRDye800 (3 nmol/mouse) in mice bearing M21 melanoma (C) is also shown. All images are normalized to the same scale. Arrows indicate tumors.

All compositions within the scope of the present invention discussed in reference to the above figures represent merely embodiments of the present invention and are not intended to individually embody the entirety of the invention. While the embodiments discussed in the above figures and the detailed description below are sufficient to teach one skilled in the art to make and use the entirety of the invention in all of its embodiments, they do not individually describe each and every possible embodiment of the invention and should not be interpreted to do so.

DETAILED DESCRIPTION

Embodiments of the present invention include imaging agents and cyclic peptides useful in imaging and/or treating tumors, compounds including the imaging agents and cyclic peptides, and methods of making and using such imaging agents and cyclic peptides.

One embodiment of the present invention relates to at least one stable cyclic polypeptide of the formula c(X$_1$X$_2$X$_3$HWGFTLX$_4$; SEQ ID NO. 4), wherein X$_1$, X$_2$, X$_3$ and X$_4$ may each be an L-amino acid, a D-amino acid, or a non-natural amino acid and one or more of amino acids $X_1$, $X_2$, $X_3$ and $X_4$ may be omitted. The peptides are cyclized through an amide bond.

These peptides bind to MMPs, such as MMP-2, MMP-8 and MMP-9, and may be stable for at least several hours in culture medium. Such peptides may also be stable for at least several hours in vivo. In a more specific embodiment, less than 50% of the peptides degrade in 24 hours either in vitro or in vivo. One specific HWGFTL (SEQ ID NO. 5) peptide within the scope of the present invention has the general formula of c(KAHWGFTLD)NH$_2$ (SEQ ID NO. 10).

These peptides may have many uses, including uses as selective inhibitors of MMPs. Inhibitory uses may form part of cancer treatment or treatment of other MMP-related diseases.

Other embodiments of the present invention relate to conjugated forms of peptides. Particular embodiments relate to conjugated forms of HWGFTL (SEQ ID NO. 5) peptides and other known MMP-targeting molecules and RGD peptides. More specifically, the peptides may be conjugated to at least one imaging agent (diagnostic agent), such as Near Infrared (NIR) imaging agents, Magnetic Resonance Imaging (MRI) imaging agents and nuclear imaging agents.

In certain embodiments of the present invention, the peptides may be conjugated to at least on NIR imaging agent. NIR imaging agents of the present invention may include dyes such as fluorophores (fluorochromes). In certain exemplary embodiments, cyanine and indocyanine derivatives may be used as NIR imaging agents. In one specific NIR imaging composition, the peptides may be conjugated to the near infrared fluorophore Cy5.5. Examples of suitable indocyanine may include ICG and its derivatives. Such derivatives may include TS-ICG, TS-ICG carboxylic acid and TS-ICG dicarboxylic acid. (See FIG. 19.) The tetrasulfonic acid group substitutions may enhance solubility of the molecule. The carboxylic acid group(s) may serve to allow labeling of biomolecules. A fluorescence spectra of TS-ICG carboxylic acid shows a excitation peak at about 765 nm and an emission peak at about 796 nm. (See FIG. 20.) A commercially available ICG derivative is IRDye800, which is available from LiCor Biosciences in Lincoln, Nebr. FIG. 21 shows the relative stability of the TS-ICG compounds when compared with IRDye800 in basic conditions (pH 8-9). Increased stability of the NIR imaging agent in basic conditions may be useful in situations where basic conditions are needed for conjugation chemistry.

In other exemplary embodiments, the peptides may be conjugated to at least one MRI imaging agent. MRI imaging agents may generally include any paramagnetic imaging agents, including, but not limited to, paramagnetic imaging agents based on liposomes or nanoparticles. In other exemplary embodiments, the MRI imaging agent may include Gd, Mn or iron oxide.

In certain exemplary embodiments, the peptides may be conjugated to at least one nuclear imaging agent. The nuclear imaging agent may generally include a radionuclide. In some embodiments, the radionuclide may include $^{18}$F, $^{131}$I, $^{124}$I, $^{125}$I, $^{111}$In, $^{99m}$Tc, $^{67}$Cu, $^{64}$Cu, $^{68}$Ga and/or combinations thereof.

In other embodiments, other imaging agents known in the art may be conjugated to the peptide for the particular imaging technique.

Methods of conjugating imaging agents known in the art or later discovered, and may be readily modified with the benefit of this disclosure to allow conjugation to cyclic peptides.

In other embodiments, the cyclic peptides may be conjugated to at least one therapeutic agent. Therapeutic agents may include chemotherapeutics. One specific chemotherapeutic that may be directly conjugated to the HWGFTL (SEQ ID NO. 5) cyclic peptides includes Cam (camptothecin). Other chemotherapeutics, such as paclitaxel and doxorubicin may also be conjugated to the HWGFTL (SEQ ID NO. 5) cyclic peptides. In other embodiments of the present invention, a chemotherapeutic may include methotrexate (MTX), an agent commonly used for cancer therapy and the treatment of rheumatoid arthritis.

One skilled in the art, with the benefit of this disclosure will recognize other suitable imaging agents and/or therapeutic agents to attach to at least one cyclic peptide ring of the present disclosure and suitable imaging and/or therapeutic techniques to use for a given application.

These imaging and therapeutic agents, may be directly or indirectly conjugated to the peptides. In certain embodiments, at least one imaging and/or therapeutic agent may directly conjugated to the peptide ring. The degree of substitution of imaging and/or therapeutic agents on the peptide ring may be limited to the number of sites on the peptide ring available for binding and/or the steric hindrances caused by the bound imaging and/or therapeutic agents. Additionally, steric hindrances that limit the ability of the peptide to bind to the $\alpha_v\beta_3$ integrin site or to MMPs may limit the number of imaging and/or therapeutic agents that can be bound to the peptide ring. In specific embodiments the peptides provide a targeting function regardless of the imaging agent, therapeutic agent, or other agent to which they are coupled either directly or indirectly.

In other embodiments of the present invention, the imaging or therapeutic agents of the present invention may be indirectly coupled to the peptides. In one embodiment, the imaging and/or therapeutic agents of the present invention may be indirectly attached through an imaging and/or therapeutic agent that is directly attached to the peptide. Through coupling of imaging and/or therapeutic agents on each other, many agents may be able to be attached to a peptide.

In other embodiments, the imaging and/or therapeutic agents may be indirectly coupled to the peptide through a linker molecule or a linker element directly coupled to the peptide. In some embodiments of the present invention, the linker molecule may include an intervening polymer. Intervening polymers may include, for example, a polymer such as poly(L-Glutamic acid) or another poly(amino acid), polyethylene glycol(PEG) and/or an aliphatic chain. In these embodiments the imaging and/or therapeutic agent may be indirectly bound to the peptide through the intervening polymer.

In other embodiments of the present invention, the linker molecule may comprise Lysine or other dual functional amino acids. In some embodiments, the Lysine may be coupled to an R group on the cyclic peptide, particularly an R group of an amino acid not directly involved in target binding. In other embodiments Lysine may be coupled on other locations of the cyclic peptide.

In some embodiments of the present invention, the linker molecule or linker element may be indirectly bound to the peptide. The linker molecule or linker element may be indirectly coupled to the peptide through another linker molecule, an imaging agent, or a therapeutic agent.

A linker molecule or linker element directly or indirectly coupled to a peptide may have additional imaging and/or therapeutic agents attached thereon. In some embodiments of the present invention, the linker molecules or linker elements may have one or more imaging agents and/or one or more therapeutic agents substituted thereon. For example, by having imaging agents and/or therapeutic agents as substituents on the polymer chain, the intervening polymer may serve as a carrier for these agents. The degree of substitution on the linker molecules or linker elements may be limited by the steric hindrance caused by the substituents. Having a high degree of substitution on the linker molecule or linker element may have the advantage of increasing the concentration of imaging and/or therapeutic agents in a particular location.

Linker molecules, such as PEG, may also be directly or indirectly coupled to cyclic peptides to inhibit filtration of the peptide compound by the kidneys. Attaching linker molecules, particularly those that substantially increase the size of the overall composition may enhance the performance of the peptide compounds in in vivo and dynamic imaging techniques.

Embodiments of the present invention also include embodiments with two cyclic peptides attached to one or more imaging and/or therapeutic agent(s). FIG. 22 represents an embodiment with two c(KRGDf; SEQ ID NO. 3) peptides, which may also be referred to as a dimeric imaging agent, as opposed to monomeric imaging agent (also shown, which has only one attached cyclic peptide). FIG. 23 shows that embodiments with dimeric imaging agents may show enhanced targeting capabilities over monomeric imaging agents. Other embodiments of the present invention may include compounds with more than two peptides.

The cyclic peptide imaging agent compositions of the present invention may be used for imaging, treatment or other uses, depending upon the molecule(s) conjugated to the cyclic peptide(s). In preferred embodiments the cyclic peptide may serve a targeting function. More specifically, the cyclic peptides may serve to target tumor cells and tumor stromal cells. However, other angiogenic-related diseases and problems may also be detected. Many such angiogenic cells and their associated diseases are known to the art and are described in further detail in P. Carmeliet, Angiogenesis in Health and Disease, *Nature Medicine,* 9:653-660 (2003).

In a specific embodiment, cyclic peptides of the present invention conjugated to NIR imaging agents are used in NIR imaging. More specifically, they may be used to detect early stage tumors such as those not detectable by MRI or CT scans and tumors less than 5 cm in diameter, 1 cm in diameter, 5 mm in diameter, or 2 mm in diameter. These cyclic peptide imaging agent compositions may also be used to detect small metastases.

For example, cyclic peptide/NIR imaging agent compositions of the present invention may be used to detect melanoma, breast cancer or sentinel lymph node metastases. In these applications especially, the light path will not be a substantially limiting factor. In applications where lack of a light path may prove problematic, the imaging agent compositions may be used with other techniques, such as laproscopic surgical techniques or endoscopy, for NIR diagnosis.

Additionally, these imaging agents may be able to detect tumors even in deep tissues without the need for surgery or endoscopy in small animals, such as mice and small pets.

In another embodiment, the cyclic peptide/NIR imaging agent compositions may be used intraoperatively, for example to define surgical margin and to detect residual tumor cells for treatment or excision.

In yet another embodiment, cyclic peptide imaging agent compositions may be used to determine the efficacy of other therapy, such as anti-MMP therapies, anti-integrin therapies and anti-angiogenic therapies.

In all embodiments of the present invention, more than one type of cyclic peptide, imaging agent, or therapeutic may be used at the same time, whether coupled in the same composition or not. This may allow treatment of different regions of a tumor with different drugs or treatment of the same tumor with different drugs. This may, for example, aid in destroying cells resistant to one type of treatment.

In diagnostic embodiments, coupling of different color imaging agents or otherwise distinguishable imaging agents to different cyclic peptides allows imaging of different markers of the tumor, or improved imaging of the tumor overall. For example, use of a c(KRGDf; SEQ ID NO. 3) peptide coupled to one NIR imaging agent along with a HWGFTL (SEQ ID NO. 5) peptide coupled to a different-colored imaging agent allows multi-color imaging of a tumor. This multi-color image may, for example, allow studies of the relationship between angiogenic molecular markers in the tumor, or indicate the overall stage and morphology of the tumor.

Use of multiple cyclic peptides as targeting agents for intraoperative NIR imaging may help ensure that residual tumor cells are removed or further treated by exposing cells not detectable by one or more of the possible cyclic peptide imaging agents.

Additional embodiments of the present invention include compositions for multiple modality imaging. Compositions for multiple modality imaging may include at least two different imaging agents, or one agent functional in at least two different types of imaging. In particular, compositions for multiple modality imaging may include at least two different imaging agents for two different types of imaging. For example, FIG. 24 shows a general representation of a cyclic peptide with both an NIR dye and a radiometal chelator. Here "R" represents a linker such as described above. The imaging composition of FIG. 24 may be used for both optical and nuclear imaging. FIG. 25 shows a representative example of such a dual modality imaging composition: $^{111}$In-DTPA-K(ICG)-c(KRGDf; SEQ ID NO. 3), where ICG may be TS-ICG or IRDye800.

FIGS. 26A AND 26B show representative examples of using such a dual modality imaging composition. In FIGS. 26A and 26B a mouse was injected with the dual modality imaging composition $^{111}$In-DTPA-K(ICG)-c(KRGDf; SEQ ID NO. 3), where ICG=IRDye800. The mouse bears both integrin positive (M21) and integrin negative (M21-L) melanoma. FIGS. 26A and 26B show that the M21 tumor is clearly visualized in both nuclear and optical images. FIG. 26A shows a nuclear gamma image of the mouse. FIG. 26B shows a NIR optical image of the same mouse. FIG. 27 shows a cut-and-count analysis of melanoma tumors in mice injected with $^{111}$In-DTPA-K(ICG)-c(KRGDf; SEQ ID NO. 3). Integrin-positive M21 tumors had a much higher intake of $^{111}$In-DTPA-K(ICG)-c(KRGDf; SEQ ID NO. 3) than integrin-negative M21-L tumors.

Additional embodiments of the present invention include a cyclic peptide composition having at least one imaging (diagnostic) agent and at least one therapeutic agent. FIG. 28 shows a general representation of a dual functional peptide with both an imaging agent and a therapeutic agent. In FIG. 28, "R" represents a linker such as described above. Various multiple functional composition, which may contain more than one type of imaging agent and/or more than one type of therapeutic agent may be created.

If a cyclic peptide composition includes both an imaging agent and a therapeutic agent, the composition may be used for both the treatment and the monitoring of the localization of the therapeutic agents and thus treatment response. This may allow both treatment and imaging of the diseased area through injection of a single composition and also may ensure that the therapeutic agent is actually delivered to the area imaged. FIG. 29 shows a representative example of cyclic peptide therapeutic agent composition and three more representative examples of dual functional cyclic peptide compositions. All compositions in FIG. 29 use the peptide c(KRGDf; SEQ ID NO. 3), but use of the HWGFTL (SEQ ID NO. 5) peptides is also possible. Structure I shows the cyclic peptide coupled with the therapeutic agent MTX. Structure II shows the cyclic peptide coupled with both the therapeutic agent MTX and the imaging agent deferoxamine, a chelator for radiometal gallium ($^{66}$Ga, $^{67}$Ga or $^{68}$Ga). Structure III shows the cyclic peptide coupled to the therapeutic agent MTX and the imaging agent ICG. Lastly, structure IV shows the cyclic peptide coupled to the therapeutic agent MTX and the radiometal chelator DTPA.

Finally, other embodiments of the present invention relate to the use of tetracycline, a known MMP-targeting molecule, and/or MMP-targeting molecules known to one skilled in the art, as a targeting agent for imaging agents or therapeutic agents. Tetracycline or MMP-targeting molecules may be used as a substitute for or in combination with the HWGFTL (SEQ ID NO. 5) cyclic peptides in all compositions, methods and uses described herein.

The following examples are provided only to illustrate certain aspects of the invention and are not intended to embody the total scope of the invention or any aspect thereof. Variations of the exemplary embodiments of the invention below will be apparent to one skilled in the art and are intended to be included within the scope of the invention.

EXAMPLE 1

General Methods and Materials

All $N^\alpha$-Fmoc-amino acids, 1-hydroxybenzotriazole (HOBt), 1-ethyl-3-(3-dimethylaminopropylcarbodiimide) (EDAC), benzotriazol-1-yl-oxy-tris-pyrrolidino-phosphonium hexafluorosulphate (PyBOP), solid support linker [4-(4-hydroxymethyl-3-methoxyphenoxy)butyric acid] (HMPB), and Trifluoroacetic acid (TFA) were purchased from Nova-biochem (San Diego, Calif.), Chem-impex International, Inc. (Wood Dale, Ill.), or Advanced Chemtech (Louisville, Ky.).

PL-DMA resin was purchased from Polymer Laboratories (Amherst, Mass.).

4-Dimethamino-pyridin (DMAP), N,N-diisopropylethylamine (DIPEA), ammonium acetate (NH$_4$OAc), triisopropylsilane (TIS), 1,3-diisopropylcarbodiimide (DIPCDI), ethylenediamine, N-hydroxysuccinimide, and triethylsilane (TES) were purchased from Aldrich Chemical Co. (St. Louis, Mo.).

Monofunctional hydroxysuccinimide ester of Cy5.5 imaging agent (Cy5.5-NHS) was purchased from Amersham Biosciences (Piscataway, N.J.).

Indocyanine green derivative, IRDye800-NHS, was obtained from Li-Cor (Lincoln, Nebr.). All solvents were purchased from VWR (San Dimas, Calif.).

Camptothecin (Cam) was purchased from Hande Tech Development Co. USA, Inc. (Houston, Tex.).

1,4,7,10-tetraazocyclododecane-1,4,7-trisacetic acid-10-acetic acid mono (N-hydroxysuccinimidyl ester) (DOTA-NHS) was purchased from Macrocyclics (Dallas, Tex.).

Analytical high-performance liquid chromatography (HPLC) was performed on a Hewlett-Packard 1090 or Agilent 1100 liquid chromatograph (Wilmington, Del.) equipped with a Vydac Peptide and Protein analytic C-18 column (Anaheim, Calif.). Preparative HPLC was carried out on a Rainin Rabbit HP equipped with a 25×25 cm Vydac Peptide and Protein C-18 column or a 25×5.5 cm Vydac Peptide and Protein C-18 column.

Matrix-assisted laser desorption ionization (MALDI) mass spectrometry was performed in the Laboratory of Proteomics in the Department of Molecular Pathology at M.D. Anderson Cancer Center (Houston, Tex.).

Fluorescence properties were measured on a Fluorolog-3 spectrophotometer (Jobin Yvon Inc., Edison, N.J.).

EXAMPLE 2

Cy5.5-RGD and IRDye800-RGD Polypeptide Synthesis

One embodiment of the present invention relates to a cyclic RGD pentapeptide c(KRGDf; SEQ ID NO. 3) conjugated to Cy5.5 imaging agent to form Cy5.5-c(KRGDf; SEQ ID NO. 3). This embodiment may be synthesized via Fmoc solid-phase chemistry followed by in solution cyclization between Arg and Lys with a head-to-tail configuration.

More specifically, peptides were synthesized on linker-PL-DMA resin using Fmoc solid phase chemistry. 4-(4-hydroxymethyl-3-methoxyphenoxy)butyric acid linker (HMPA) was used for solution phase cyclization. HMPA (3 eq) was attached to PL-DMA resin, which was treated with ethylenediamine overnight. The peptide was cleaved from the support with 1% TFA in DCM with all side chain protecting groups intact. The head-to-tail cyclization was then carried out in DMF using PyBOP (3 eq), HOBt (3 eq), and DIPEA (6 eq) as coupling agents. After removal of all solvents the residue was dissolved with ethyl acetate and washed with 5% NaHCO$_3$, 2% KHSO$_4$, and brine. All side-chain protecting groups were deprotected in TFA/H$_2$O/TES (95/1/4, v/v/v).

Each cyclic peptide was purified by reverse phase HPLC eluted with H$_2$O/acetonitrile containing 0.1% TFA, and validated by analytic HPLC and MALDI mass spectrometry.

A solution of Cy5.5-NHS (1 eq) or IRDye800-NHS (1 eq) and c(KRGDf; SEQ ID NO. 3) (1.3 eq.) in dimethylformamide/DIPEA (10/1, v/v) was stirred at room temperature overnight. FIG. 30 represents a synthesis scheme for Cy5.5-c(KRGDf; SEQ ID NO. 3). After solvent was removed under vacuum, the compound was purified by reverse phase HPLC eluted with a 0.01 M solution of NH$_4$OAc in water/acetonitrile and was lyophilized. The products were validated by analytic HPLC and MALDI mass spectrometry.

Although Cy5.5 and IRDye800 were chosen for use in this specific example, this choice largely reflects its commercial availability. Use of other cyanine and indocyanine derivatives is also possible. Some different cyanine or indocyanine derivatives may be better in certain applications. For example, indocyanine green derivatives tend to increase tissue penetration of the conjugated molecule and this improves NIR images.

The structure of representative cyclic polypeptides is shown in FIG. 30. MALDI mass spectrometry and HPLC data of cyclic peptide alone or coupled to Cy5.5 are summarized in Table 1.

TABLE 1

MALDI mass spectrometry and HPLC data of cylcic peptides cyclic peptides.

| Cyclic Peptides | Molecular Formula | Mass Spectrometry | | HPLC Retention time*(min) |
|---|---|---|---|---|
| | | Calculated | Observed | |
| c(KRGDf; SEQ ID NO. 3) | $C_{27}H_{41}N_9O_7$ | 603.3129 | 604.3563 | 9.05 |
| Cy5.5-c(KRGDf; SEQ ID NO. 3) | $C_{68}H_{84}N_{11}O_{20}S_4^+$ | 1502.4777 | 1053.5286 | 19.28 |

*Samples were eluted with acetonitrile containing 0.1% TFA varying from 1% to 40% in 30 minutes.

EXAMPLE 3

In Vitro Cy5.5-c (KRGDf; SEQ ID NO. 3) Studies

KS1767 sarcoma cells were maintained at 37° C. in a humidified atmosphere containing 5% $CO_2$ in Dulbecco's Modified Eagle's Medium/Nutrient Mixture F-12 Ham (DMEM/F12) and 10% FBS (Gibco, Grand Island, N.Y.).

Blockage studies were conducted using these cells to demonstrate that Cy5.5-c(KRGDf; SEQ ID NO. 3) may be used in vitro to bind to $\alpha_v\beta_3$ integrin. Cells were seeded on cover slips in 24-well plates (Becton Dickinson Labware, Franklin Lakes, N.J.) and incubated in DMEM/F12 culture medium (0.5 ml/well) overnight. Unconjugated c(KRGDf; SEQ ID NO. 3) was added to the culture medium at various concentrations. Cy5.5-c(KRGDf; SEQ ID NO. 3) was added one hour later to each well at a concentration of 6 µM. Cells were washed twice with PBS and incubated in a solution of Sytox Green in 95% ethyl alcohol (1 µM, Molecular Probe, Eugene, Oreg.) for 15 minutes to fix and stain cell nuclei. Cells were washed again with PBS and the cover slips were mounted for microscopic examination using a DMR microscope (Leica Microsystems Inc., Bannockburn, Ill.). The microscope was equipped with a 75W Xenon lamp, 775 nm/845 nm, 560 nm/645 nm, and 480 nm/535 nm (Excitation/emission) filters (Chroma Technology Corp., Brattleboro, Vt.), a Hamamatsu B/W Chilled CCD Camera (Hamamatsu Photonics K.K., Hamamatsu City, Japan), and an Image-Pro Plus 4.5.1 software (Media Cybernetics, Silver Spring, Md.). In the multiple staining images, Cy5.5 was pseudocolored red and Sytox Green was green.

Figure 3:
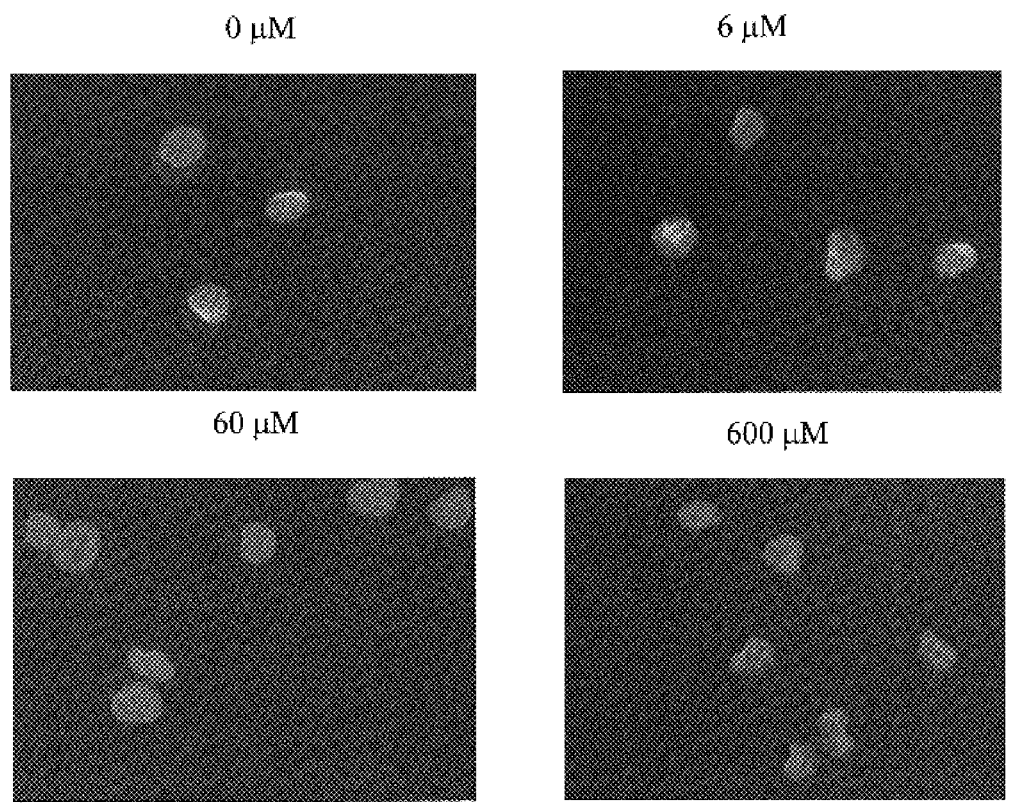
FIG. 3 shows in vitro binding of Cy5.5-c(KRGDf; SEQ ID NO. 3) to KS1767 cells. The cells were incubated with the indicated concentrations of c(KRGDf; SEQ ID NO. 3) and with Cy5.5-c(KRGDf; SEQ ID NO. 3) at a concentration of 6 μM for 10 minutes. Cy5.5 imaging agent is red. Syntox Green labeled nuclei are green. Original magnification is 60×.

In vitro binding of Cy5.5-c(KRGDf; SEQ ID NO. 3) to $\alpha_v\beta_3$ was demonstrated by a dose-dependent blockage of Cy5.5-c(KRGDf; SEQ ID NO. 3) binding to KS1767 cells, which express $\alpha_v\beta_3$ integrin, by c(KRGDf; SEQ ID NO. 3). (See FIG. 3.)

A Cell Adhesion Assay was additionally performed. KS1767 cells were seeded in DMEM/F12 culture medium supplemented with 10% fetal bovine serum for 24 hr. Cells ($1\times10^5$) with different concentrations of c(KRGDf; SEQ ID NO. 3) or Cy5.5-c(KRGDf; SEQ ID NO. 3) were added to vitronectin-coated microliter wells under serum-free conditions and incubated at 37° C. for 1 hr. After washing steps, the bound cells were stained with 5% crystal violet, followed by addition of 0.1M HCl to each well. The concentrations of crystal violet were determined by UV/V is absorption at 627 nm. $IC_{50}$ values were estimated from the dose-activity curves.

As shown in FIG. 31, Cy5.5-c(KRGDf; SEQ ID NO. 3), IRDye800-c(KRGDf; SEQ ID NO. 3), and c(KRGDf; SEQ ID NO. 3) inhibited adhesion of KS1767 cells to vitronectin-coated microplate wells in a dose-dependent manner. The $IC_{50}$ values for Cy5.5-c(KRGDf; SEQ ID NO. 3), IRDye800-c(KRGDf; SEQ ID NO. 3), and c(KRGDf; SEQ ID NO. 3) were estimated to be 1.11, 2.58, and 2.47 µM, respectively.

FIG. 31 shows the dose-dependent inhibition of adhesion of KS1767 cells to vitronectin-coated microplate wells by c(KRGDf; SEQ ID NO. 3) and its NIR dye imaging agents. Ac-A-c(CNGRC)-G was a control cyclic pentapeptide that does not bind to integrin $\alpha_v\beta_3$. The data are presented as mean and standard error of mean from triplicate experiments.

EXAMPLE 4

In Vivo Cy5.5-c(KRGDf; SEQ ID NO. 3) and IRDye800-c(KRGDf; SEQ ID NO. 3) Studies Cy5.5-c(KRGDf; SEQ ID NO. 3) may be used in near infrared (NIR) imaging. Mice inoculated with KS1767 were used for in vivo NIR studies. The mice were four to six week-old athymic nude mice (18-22 g, Harlan Sprague Dawley, Inc. Indianapolis, Ind.) which were housed 5 per cage and fed with sterilized pellet chow (Harlan Sprague Dawley) and sterilized water. The animals were maintained in a pathogen-free mouse colony in the Department of Veterinary Medicine at the University of Texas M.D. Anderson Cancer Center. All experiments were performed in accordance with the guidelines of the Institutional Animal Care and Use Committee.

Tumor cells for use in the animals were harvested near confluence by incubation with 0.05% trypsin-EDTA. Cells were pelleted by centrifugation at 450×g for 5 minutes and resuspended in sterile PBS. $2-3\times10^5$ cells/animal were implanted subcutaneously into the chest wall or hind legs of the mice. Imaging studies were performed when tumors reached 4-6 mm in average diameter.

In vivo fluorescence imaging was accomplished by illuminating the animal with light from a laser diode (35 mW) expanded to an approximate 8 cm diameter circular area. The fluorescent light re-emitted from the animal was collected by an image intensifier (model FS9910C, ITT Night Vision, Roanoke, Va.) lens-coupled to a CCD camera (model CH350, Photometrics, Tucson, Ariz.). The imaging was designed so that the field of view could be varied from 3×3 cm to over 12×12 cm by varying the image distance of the 50 mm lens used to focus the image onto the photocathode of the intensifier. The lens was fitted with a holographic notch-plus filter (660 nm center wavelength; Kaiser Optical Systems, Inc., Ann Arbor, Mich.) and a bandpass filter (710 nm center wavelength) to reject back-scattered and reflected excitation photons. Image acquisition was accomplished using V++ software (Digital Optics, Auckland, New Zealand) and the obtained images were stored in uncompressed tagged image file format (tiff). Data processing and analysis were accomplished using Matlab software (The MathWorks, Inc., Natick, Mass.). For all imaging sessions, the image acquisition parameters were kept constant, and each image required 800 ms of camera integration.

For dynamic in vivo fluorescence imaging, mice were anesthetized with an i.p. injection of 50 mg/kg pentobarbital, and a catheter was placed in the tail vein for i.v. injection of NIR dyes. A white-light image of the animal was obtained using a low-power lamp as a white light source with holographic and interference filters removed. Fluorescence images were then acquired as a function of time following administration of Cy5.5 (6 nmol per/mouse) or Cy5.5-c (KRGDf; SEQ ID NO. 3) (6 nmol per/mouse). For blocking studies, c(KRGDf; SEQ ID NO. 3) (600 nmol/mouse) was injected intravenously at 1 hr and 24 hr prior to the injection of Cy5.5-c(KRGDf; SEQ ID NO. 3). The acquisition time was 800 ms. Images were obtained every 6 seconds (s) for up to 20 minutes (min) following injection of each imaging agent. Each mouse was imaged again 24 hr after contrast injection.

Two regions of interest (ROI) were selected for quantitative analyses. One ROI was located entirely within the circumference of the tumor, and the other, of approximate equivalent size, defined a symmetric region of normal tissue located opposite the tumor site. (See FIG. 32A.) Utilizing Matlab software, the mean of the fluorescence intensity within each ROI was computed for every fluorescence image acquired. Data were acquired from the tumor ROI. (See FIG. 32B.) Data were acquired from normal muscle ROI. (See FIG. 32C.) These data were then used to generate curves of mean fluorescence intensity versus time for each imaging study. The symbols denote experimental measurements while the solid line denotes the corresponding least-squares fit. Animals were injected with Cy5.5-c(KRGDf; SEQ ID NO. 3) alone (6 nmol) (□), or Cy5.5-cc(KRGDf; SEQ ID NO. 3) 1 hr (○) and 24 hr (◊) after the injection of unconjugated c(KRGDf; SEQ ID NO. 3) peptide (600 nmol).

In Vivo NIR Imaging

FIGS. 4A and 4B show representative in vivo imaging of KS1767 tumors 24 hours after subcutaneous inoculation following intravenous injection of Cy5.5-c(KRGDf; SEQ ID NO. 3) at a dose of 6 nm/mouse. The imaging study was performed when the tumor reached about 4-5 mm in diameter. The tumors at this size were not visible in the bright line image (FIG. 4A), but NIR images clearly showed targeting of Cy5.5-c(KRGDf; SEQ ID NO. 3) to the tumors. (See FIG. 4B.) The NIR imaging findings were confirmed after the mouse was euthanized and the skin removed.

Figure 5:
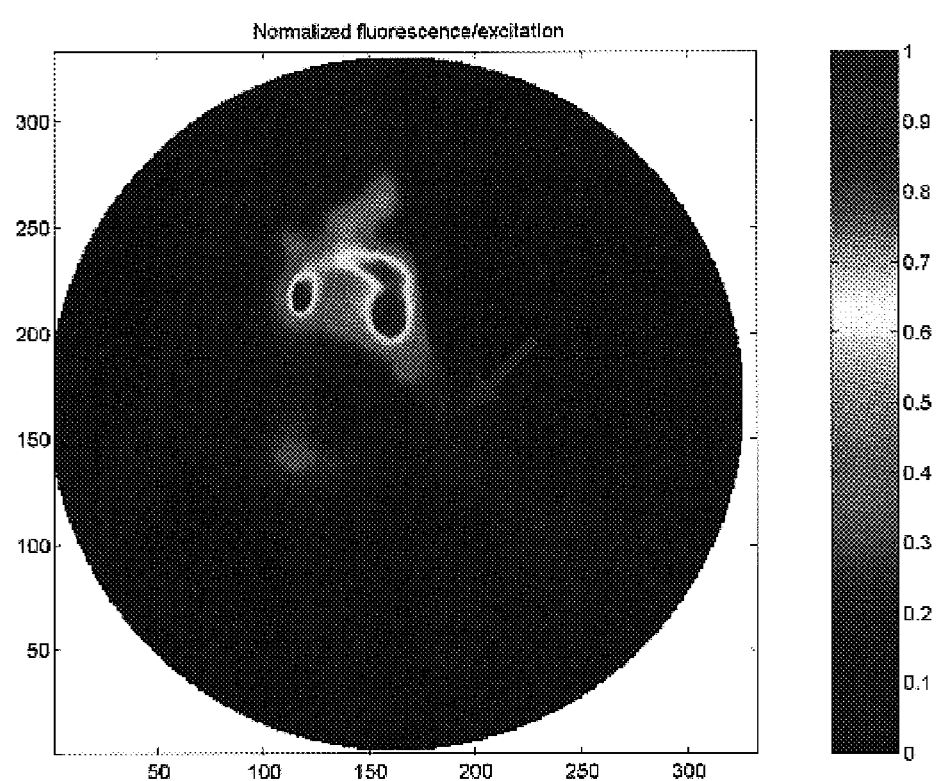
FIG. 5 shows a representative in vivo NIR image of subcutaneous KS1767 tumors 24 hours after injection of Cy5.5 alone at a dose of 6 nmol/mouse. Arrows indicate tumors.

These in vivo effects were shown to be a specific targeting effect of the polypeptide. An image of a KS1767 tumor-bearing mouse injected with only Cy5.5 shows almost no optical activity uptake in the tumor as compared to background. (See FIG. 5.) Moreover, pretreatment with 100-fold of c(KRGDf; SEQ ID NO. 3) injected 1 hour before the administration of Cy5.5-c(KRGDf; SEQ ID NO. 3) blocked the uptake of fluorophores in KS1767 tumors. (See FIGS. 6A, 6B and 33.) These results suggest that Cy5.5-c(KRGDf; SEQ ID NO. 3) selectively targets tumors with $\alpha_v\beta_3$ integrin receptors and that Cy5.5-c(KRGDf; SEQ ID NO. 3) may be used for non-invasive imaging of $\alpha_v\beta_3$ integrin expression.

Fluorescence microscopic images of excised tumor and muscle tissue immediately adjacent to the tumor confirmed that Cy5.5-c(KRGDf; SEQ ID NO. 3) was localized to the tumor, but not to the muscle cells. (See FIG. 34.)

Similar results were observed with IRDye800-c(KRGDf; SEQ ID NO. 3) in human melanoma xenograft models. Mice bearing integrin-positive M21 melanoma, but not those bearing integrin-negative M21-L melanoma, were clearly visualized 24 hr after intravenous injection of IRDye800-c (KRGDf; SEQ ID NO. 3). IRDye800 itself did not have detectable signal in the same M21 tumors. (See FIG. 35.) The tumor-to-background ratios for IRDye800-RGD imaging agent composition in mice with M21 tumors and mice with M21-L tumors were 1.7 and 1.1, respectively, as determined from the fluorescence intensity measured in the region-of-interest.

Dynamic NIR Imaging

Profiles of fluorescence intensity as a function of time were obtained from dynamic imaging data (See FIGS. 32A-C). The circles in FIG. 32A indicate the region of interest for the tumor and for the normal muscle used to generate intensity values. The rate of uptake of Cy5.5-c (KRGDf; SEQ ID NO. 3) in KS1767 tumors was faster than the rate of its uptake in the muscle (See FIGS. 32B and 32C), and more dye was taken up by the tumor. Preinjection of c(KRGDf; SEQ ID NO. 3) blocked the uptake of Cy5.5-c (KRDGf) in the tumor when the interval between the injections of these two agents was 1 hr. However, when the interval between the injections of c(KRGDf; SEQ ID NO. 3) and Cy5.5-c(KRGDf; SEQ ID NO. 3) was increased to 24 hr, the rate of Cy5.5-c(KRGDf; SEQ ID NO. 3) uptake in the tumor was partially recovered. (See FIGS. 32A-C).

EXAMPLE 5

Cyclic HWGFTL (SEQ ID NO. 5) Polypeptide Synthesis

Cyclic HWGFTL (SEQ ID NO. 5) polypeptides of the formula $c(X_1X_2X_3HWGFTLX_4$; SEQ ID NO. 4), wherein $X_1$, $X_2$, $X_3$ and $X_4$ may each be an L-amino acid, a D-amino acid, or a non-natural amino acid and one or more of amino acids $X_1$, $X_2$, $X_3$ and $X_4$ may be omitted, were synthesized on solid support or in solution. For both approaches, the peptide was originally synthesized in linear form on a solid support. Appropriate linkers were attached to ethylenediamine-treated PL-DMA resin. Peptides were synthesized on linker-PL-DMA resin using Fmoc solid phase chemistry. A 4-(4-hydroxymethyl-3-methoxyphenoxy)butyric acid linker was used for solution phase cyclization. The peptide was cleaved from the support with 1% TFA in DCM with all side chain protecting groups intact.

Cyclization in solution was carried out in DMF (1 mM) using 3 mM PyBOP/HOBt/DIPEA. After removal of all solvents, the residue was dissolved with ethyl acetate and washed with 5% NaHCO$_3$, 2% KHSO$_4$, and brine. All side-chain protecting groups were deprotected in TFA/H$_2$O/ TES (95/1/4, v/v/v). The resulting peptide exhibited head-to-tail cyclization.

4-Hydroxymethylphenoxyacetic acid and Fmoc-Rink linkers were used for solid phase cyclization, which resulted in side chain-to-side chain or side chain-to-tail linkages. The former linker was used for forming a COOH terminus, the later one was used for preparing the CONH$_2$ terminus. After the protecting groups of side chains on termini were removed with TFA/DCM/TIS (1/94/5, v/v/v), the side chain to side chain cyclization was performed in DMF (1 mM) using 3 mM PyBOP/HOBt/DIPEA. The side chain to tail cyclization between the β-carboxyl group of Asp and the N-terminus was performed in DMF. Cleavage of the cyclic peptide from the solid phase and deprotection was achieved simultaneously with TFA/H$_2$O/TES (95/1/4, v/v/v).

To prepare Cy5.5-conjugated forms of the cyclic peptides, a solution of Cy5.5—NHS (1 eq) and a cyclic peptide (1.3 eq) in DMF/DIPEA (10/1, v/v) was stirred at room temperature overnight. After all solvents and by-products were removed under vacuum, the compound was purified by reverse phase HPLC eluted with a 0.01 M solution of NH$_4$OAc in water/methanol. The products were validated be analytic HPLC and MALDI mass spectrometry.

As noted above in Example 2 with respect to c(KRGDf; SEQ ID NO. 3) imaging agents, cyanine and indocyanine derivatives other than Cy5.5 may be used as the NIR imaging agent. Both NIR dye and radionuclides such as $^{18}$F, $^{131}$I, $^{124}$I, $^{125}$I, $^{111}$In, $^{99}$Tn, $^{111}$In, $^{99m}$Tc, $^{67}$Cu, $^{64}$Cu, and $^{68}$Ga may be conjugated to multiple modality imaging compositions.

Each cyclic peptide was purified by reverse phase HPLC eluted with H$_2$O/acetonitrile containing 0.1% TFA and validated by analytic HPLC and MALDI mass spectrometry. See Table 2.

TABLE 2

MALDI Mass Spectrometry and HPLC Data of Cyclic Peptides

| Cyclic Peptides[1] | Mass Spectrometry | | | HPLC |
| --- | --- | --- | --- | --- |
| | Molecular Formula | Calculated | Observed (M + 1) | Retention Time[2](min) |
| c(ATAHWGFTLβA; SEQ ID NO. 6) (h-t) | $C_{51}H_{69}N_{13}O_{12}$ | 1055.5189 | 1056.5139 | 15.52 |
| c(ATTHWGFTLD; SEQ ID NO. 7) (sc-t) | $C_{53}H_{72}N_{14}O_{14}$ | 1128.5352 | 1129.5621 | 14.49 |
| c(KTTHWGFTLD; SEQ ID NO. 8) (sc-t) | $C_{56}H_{78}N_{14}O_{15}$ | 1186.5771 | 1187.6589 | 16.13 |
| c(KTAHWGFTLD)NH$_2$ (SEQ ID NO. 9) (sc-t) | $C_{55}H_{77}N_{15}O_{13}$ | 1155.5825 | 1156.5230 | 14.00 |
| c(KAHWGFTLD)NH$_2$ (SEQ ID NO. 10) (sc-sc) | $C_{51}H_{70}N_{14}O_{11}$ | 1054.5349 | 1055.5573 | 13.88 |
| c(KAHWGFTLD; SEQ ID NO. 10) (sc-sc) | $C_{51}H_{69}N_{13}O_{12}$ | 1055.5189 | 1056.5907 | 12.79 |
| Cy5.5-c(KAHWGFTLD)NH$_2$ (SEQ ID NO. 10) | $C_{92}H_{113}N_{16}O_{24}S_4^+$ | 1953.6996 | 1954.7416 | 15.32 |
| AcE(G-Cam)-c(KAHWGFTLD)NH$_2$ (SEQ ID NO. 10) | $C_{80}H_{96}N_{18}O_{19}$ | 1612.7099 | 1613.7725 | 17.79 |
| c(KYHWGFTLD)NH$_2$ (SEQ ID NO. 11) (sc-sc) | $C_{37}H_{74}N_{14}O_{12}$ | 1146.5611 | 1147.5582 | 14.30 |
| Cy5.5-c(KYHWGFTLD)NH$_2$ (SEQ ID NO. 11)- | $C_{98}H_{117}N_{16}O_{25}S_4^+$ | 2045.7259 | 2046.7469 | 14.23 |

[1]h-t indicates a heat-to-tail linkage. sc-t indicates a side chain-to-tail linkage. sc-sc indicates as side chain-to-side chain linkage.
[2]Samples were eluted with acetonitrile containing 0.1% TFA varying from 10% to 50% in 30 minutes.

EXAMPLE 6

Cyclic HWGFTL (SEQ ID NO. 5) Polypeptide Stability Assay

The stability of a representative HWGFTL (SEQ ID NO. 5) cyclic peptide of the present invention, c(ATTHWGFTLβA; SEQ ID NO. 2), in serum-containing culture media was compared to that of c(CTTHWGFTLC; SEQ ID NO. 1) of Pasqualini at 25° C.

Each test peptide was incubated in a serum-containing culture medium (Dulbecco's Modified Eagle's Medium/Nutrient Mixture F-12 Ham and 10% FBS) (1 mg/ml) at 25° C. At various time intervals, aliquots of peptide solution (50 μL) were withdrawn and subjected to HPLC analysis. The percentage of remaining intact peptide was recorded as a function of time.

Figure 1:
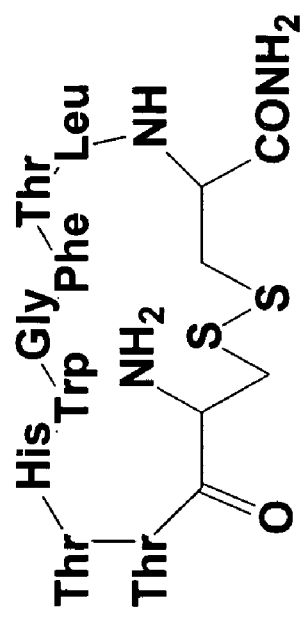
FIG. 1 shows the structure of c(CTTHWGFTLC; SEQ ID NO. 1) and the $IC_{50}$ (50% inhibitory concentration; the concentration at which the structure inhibits 50% of the activity of MMP-2) of c(CTTHWGFTLC; SEQ ID NO. 1), as described by Pasqualini et al.
Figure 2:
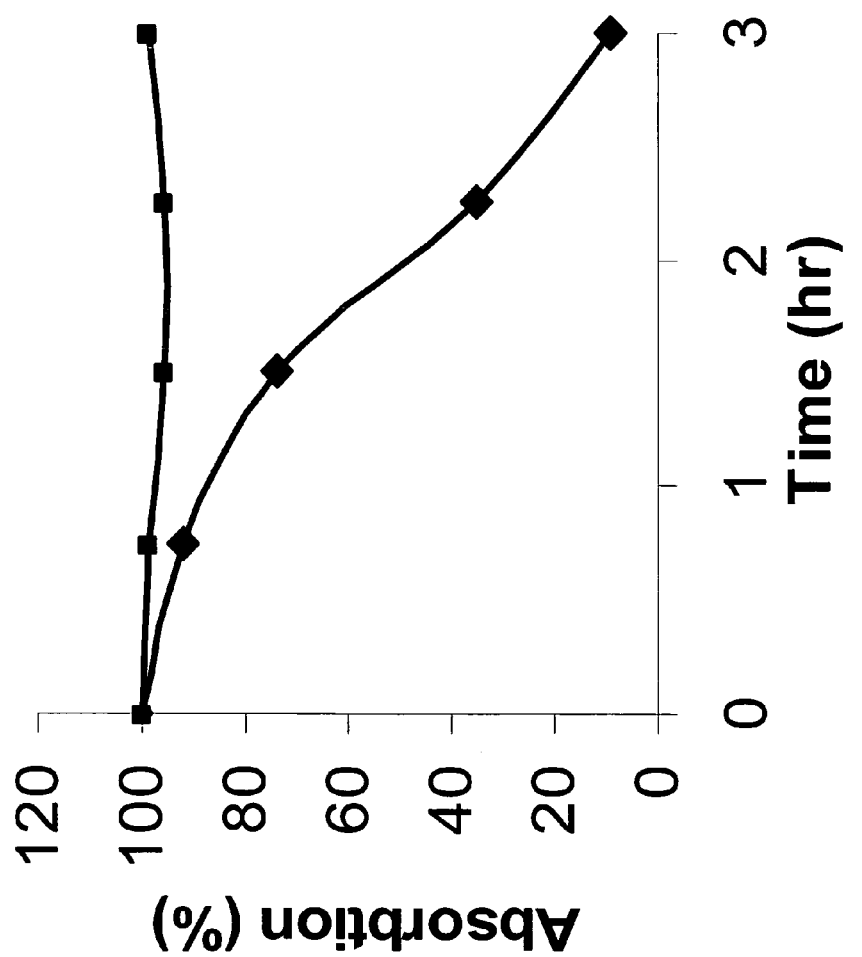
FIG. 2 graphically depicts the stability of c(CTTHWGFTLC; SEQ ID NO. 1) of FIG. 1 (bottom line with diamonds) and the c(ATTHWGFTLβA; SEQ ID NO. 2) with amide linkage, according to an embodiment of the present invention (top line with squares) in serum-containing culture medium at 25° C.

Whereas more than 90% of c(CTTHWGFTLC; SEQ ID NO. 1) peptide was degraded after only 3 hours, no apparent degradation of c(ATTHGWFTLβA) was noted under the same conditions. See FIG. 2. In fact, no degradation of c(ATTHWGFTLβA; SEQ ID NO. 2) was noted over the course of the study (5 days). Other HWGFTL (SEQ ID NO. 5) peptides of the present invention exhibited similar behavior.

EXAMPLE 7

Cyclic HWGFTL (SEQ ID NO. 5) Polypeptide Inhibition of MMP-2

The enzyme inhibition activity of various cyclic HWG polypeptides was studied using a biotinylated gelatinase substrate cleavage assay according to the manufacturer suggested procedures (Chemicon, Temecula, Calif.). Briefly, each of the test compounds was incubated with pre-activated MMP-2 (5 ng/ml) for 60 minutes at 37° C. at increasing concentration of the peptide. Subsequently, the MMP-2 solution was incubated with biotinylated gelatin (~300 mg/ml) at 37° C. for 60 minutes. Samples were transferred to biotin-binding plates pre-coated with streptavidin. Following a 30-min incubation at 37° C., plates were extensively washed and further incubated with streptavidin-HRP solution. The HRP activity was measured with HRP substrate. The plate was read at 450 nm in a microliter plate reader. The data were expressed as percentage of enzyme activity as compared to no-inhibitor controls. IC$_{50}$ was defined as the peptide concentration at which 50% of enzyme activity was inhibited.

EXAMPLE 8

Further Studies with c(KAHWGFTLD)NH$_2$ (SEQ ID NO. 10)

Figure 7:
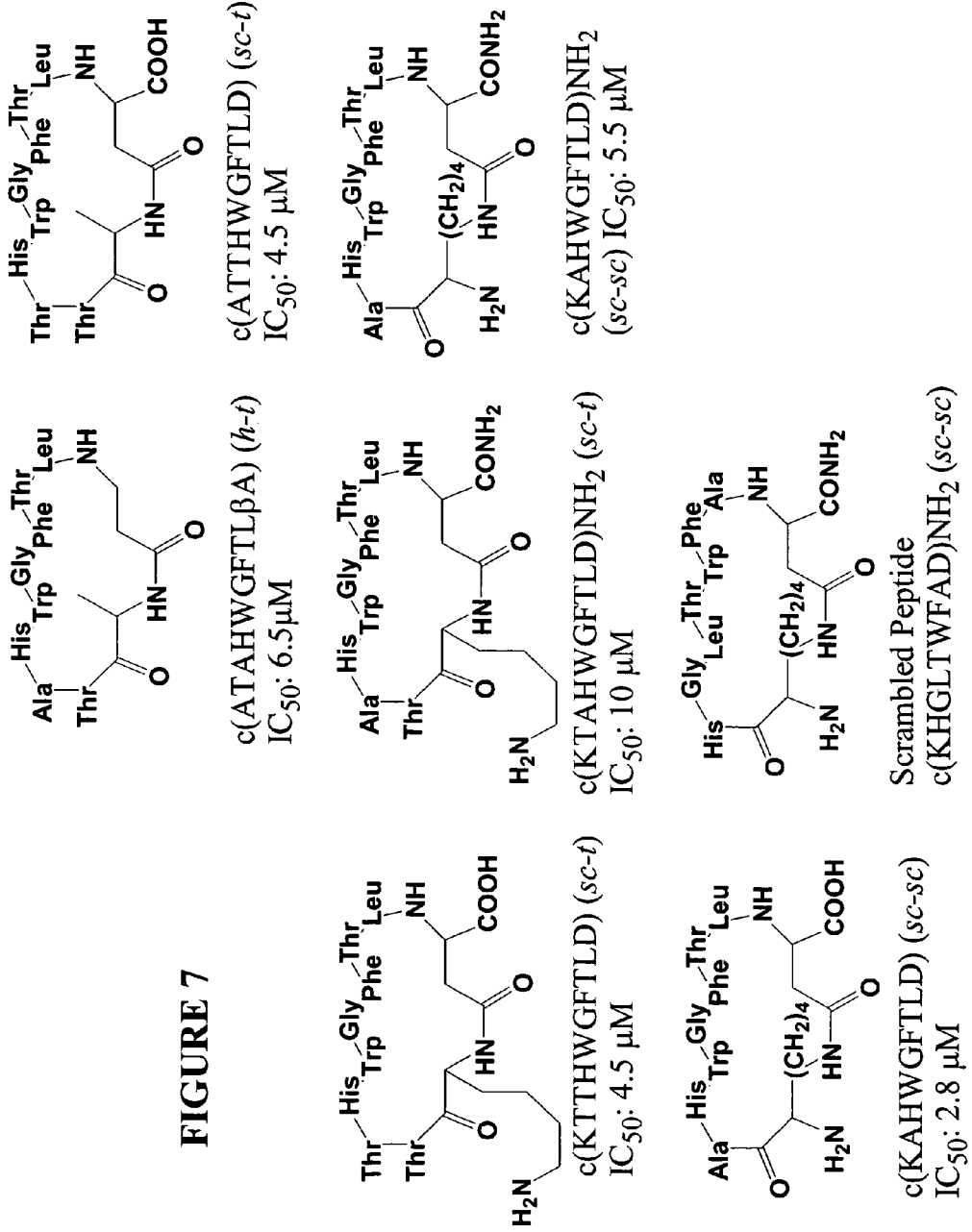
FIG. 7 illustrates the structure and $IC_{50}$ (for inhibition of MMP-2 activity) of several cyclic HWGFTL (SEQ ID NO. 5) peptides. In the figure, "sc-sc" designates a cyclic polypeptide cyclized through a linkage of the side chain of one amino acid to the side chain of another amino acid. "sc-t" designates a cyclic polypeptide cyclized through a linkage of the side chain of one amino acid to the amino terminus of another amino acid. "h-t" designates a cyclic polypeptide cyclized through a linkage of the amino terminus of one amino acid to the carboxy terminus of another amino acid.
Figure 8:
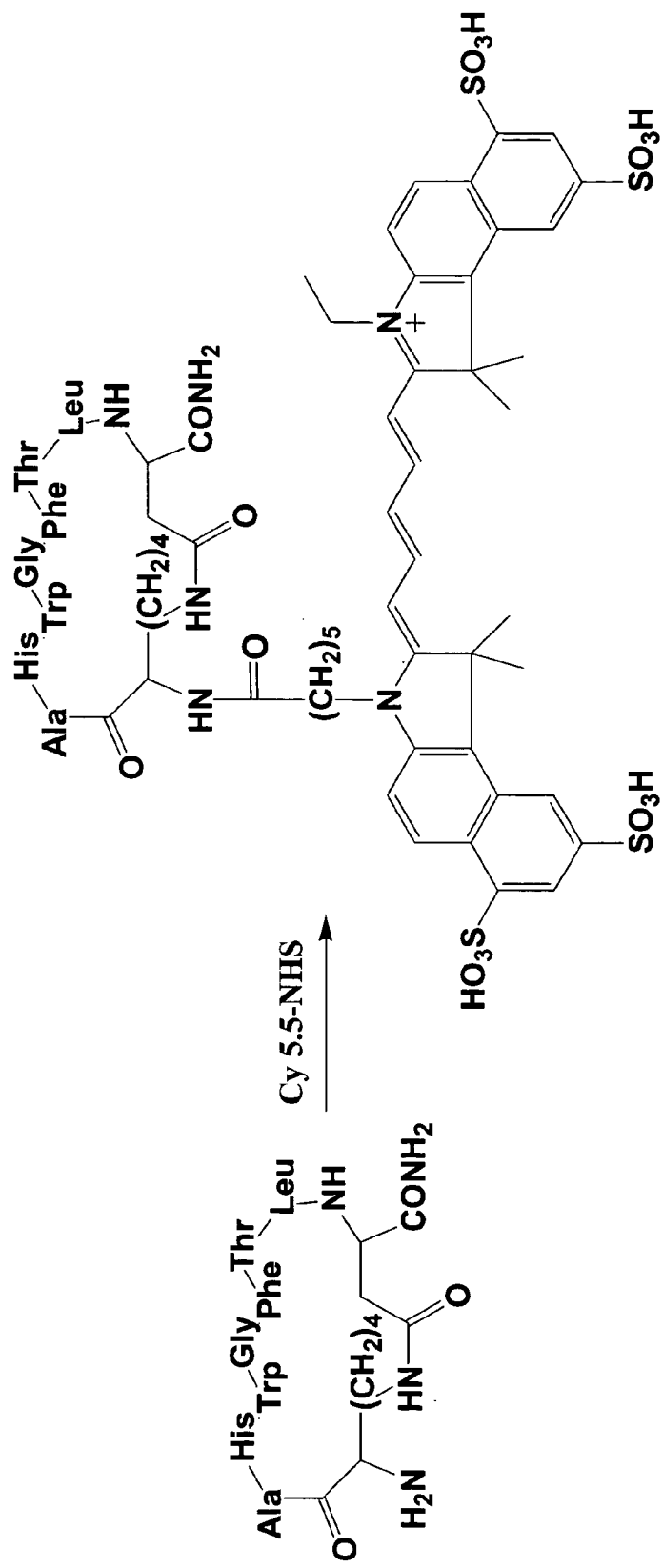
FIG. 8 shows a method of synthesis of Cy5.5-c(KAHWGFTLD)NH$_2$ (SEQ ID NO. 10).
Figure 9:
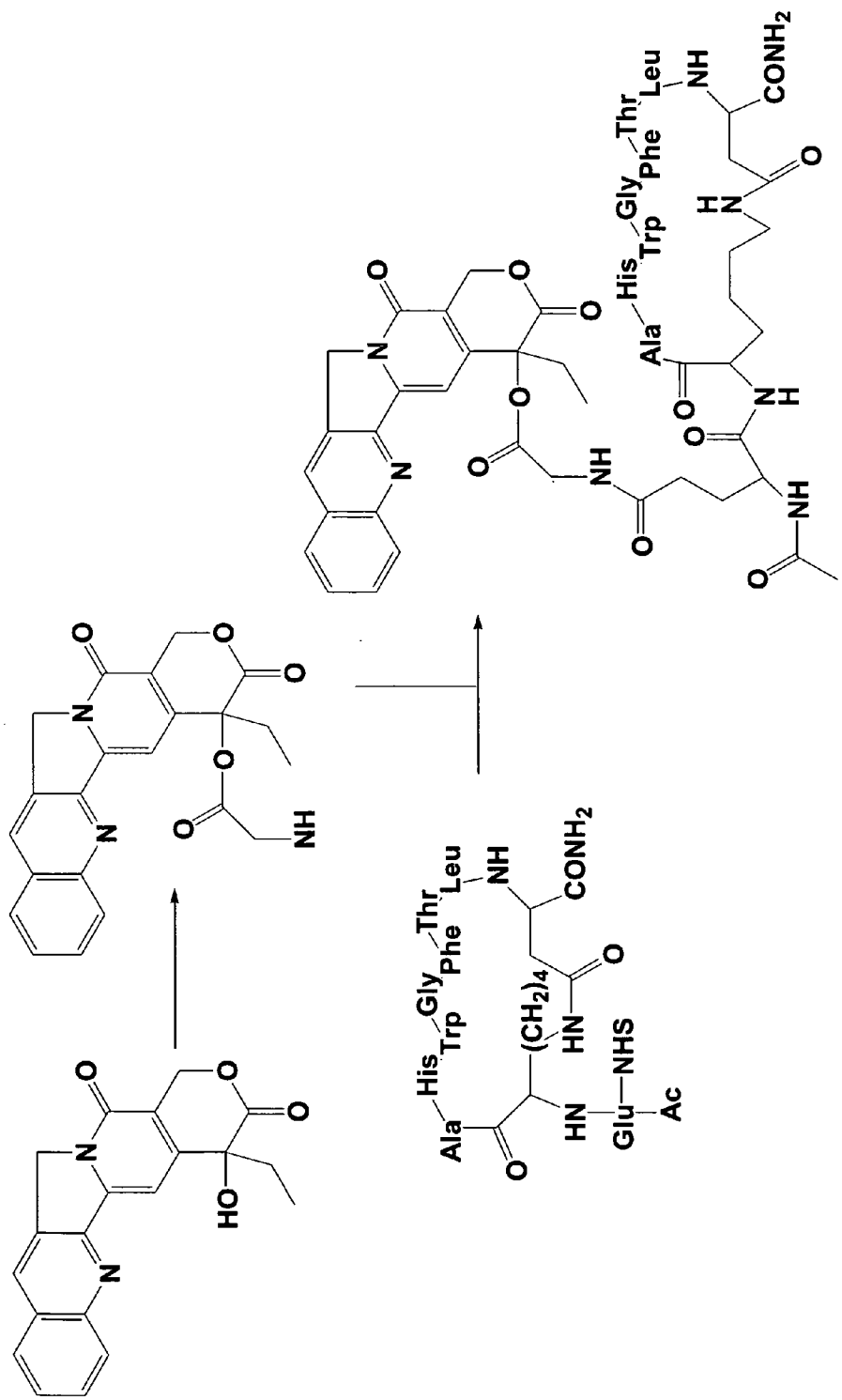
FIG. 9 shows a method of synthesis of AcE(G-Cam)-c(KAHWGFTLD)NH$_2$ (SEQ ID NO. 10). "Cam" designates camptothecin.

The HWGFTL (SEQ ID NO. 5) peptides of the present invention containing carboxyl, amino, hydroxyl and/or sulfhydryl functional groups may be used for coupling with diagnostic of therapeutic agents. c(KAHWGFTLD)NH$_2$ (SEQ ID NO. 10) with a side chain-to-side chain linkage (shown in FIG. 7) was selected for further evaluation based upon its MMP-2 inhibition activity ($IC_{50}$=5.5 μM), convenience of synthesis, solubility in aqueous solution, and the presence of an amino functional group. A near infrared fluorophore Cy5.5 was conjugated to c(KAHWGFTLD)NH$_2$ (SEQ ID NO. 10) through an activated ester of Cy5.5 (Cy5.5—NHS) (See FIG. 8). A model chemotherapeutic agent, Cam, was also conjugated to AcEc(KAHWGFTLD)NH$_2$ (SEQ ID NO. 10) through a Gly linker to the side chain of Glu. (See FIG. 9.) HPLC and MALDI mass spectrometry characteristics of these imaging agents are summarized in Table 2. An analogue of c(KAHWGFTLD)NH$_2$ (SEQ ID NO. 10) where amino acid Ala was replaced with Tyr, c(KYHWGFTLD)NH$_2$ (SEQ ID NO. 11) (side chain-to-side chain linkage), was also synthesized. This peptide and its imaging agent with Cy5.5 (Table 2) may be radiolabeled (e.g. with $^{131}$I, $^{124}$I, $^{125}$I, $^{90}$Y, etc.) for nuclear imaging and radiotherapy applications.

EXAMPLE 9

In Vitro Cyclic HWGFTL (SEQ ID NO. 5) Polypeptide Tumor Cell Binding Studies

All human tumor cell-lines were obtained from American Type Culture Collection (Rockville, Md.) and were maintained at 37° C. in a humidified atmosphere containing 5% $CO_2$ in Dulbecco's Modified Eagle's Medium/Nutrient Mixture F-12 Ham (DMEM/F12) and 10% FBS (Gibco, Grand Island, N.Y.).

Cells were seeded on cover slips in 24-well plates (Becton Dickinson Labware, Franklin Lakes, N.J.) and incubated in DMEM/F12 culture medium (0.5 ml/well) overnight. Cy5.5 and Cy5.5-HWG polypeptide imaging agents were added into each well at the indicated concentrations. For the blocking study, doxycycline was added to the culture medium followed by the addition of Cy5.5-HWG polypeptide imaging agent 1 hour later. After an incubation period of 5-60 minutes at 37° C., cells were washed twice with PBS and incubated in a solution of Sytox Green in 95% ethyl alcohol (1 μM, Molecular Probe, Eugene, Oreg.) for 15 minutes to fix and stain cell nuclei. For staining of MMP expression, cells that were pretreated with Cy5.5-HWG polypeptide and stained with Sytox Green were incubated with anti-MMP antibody (Sigma) (1 mg/ml; 1:200 dilution) for 1 hour at room temperature. The cells were then washed and incubated with Texas Red conjugated go at anti-rabbit IgG (Molecular Probe, 4 μg/ml) at room temperature for 1 hour. Cells were washed again with PBS and the cover slips were mounted for microscopic examination using a DMR microscope (Leica Microsystems, Inc., Brannockburn, Ill.). The microscope was equipped with a 75W Xenon lamp, 775 nm/845 nm, 560 nm/645 nm, and 480 nm/535 nm (Excitation/emission) filters (Chroma Technology Corp., Brattleboro, Vt.), a Hamamatsu B/W Chilled CCD camera (Hamamatsu Photonics K.K., Hamamatsu City, Japan), and Image-Pro Plus 4.5.1 software (Media Cybernetics, Silver Spring, Md.). In the multiple staining images, Cy5.5, MMPs, and Sytox Green were pseudocolored red, green, and blue, respectively.

Figure 10:
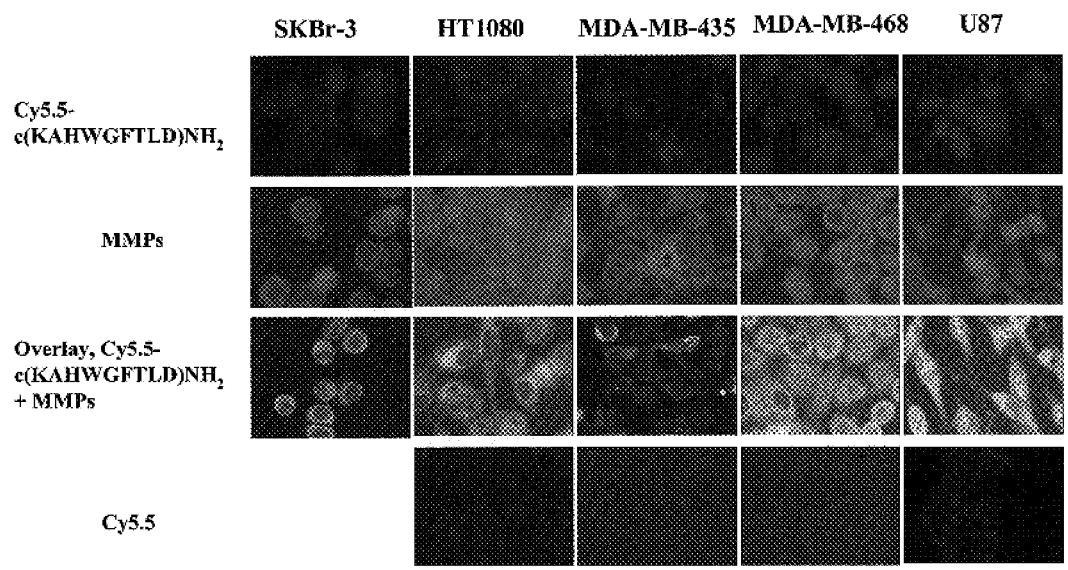
FIG. 10 shows the results of in vitro assays with Cy5.5-c(KAHWGFTLD)NH$_2$ (SEQ ID NO. 10). Tumor cells were incubated with Cy5.5-c(KAHWGFTLD)NH$_2$ (SEQ ID NO. 10) (10 μM) or Cy5.5 (50 μg/ml, 56 μM) at 37° C. for 5 minutes. The cells were then washed and stained with Sytox Green for nuclei and with anti-MMP-2, anti-MMP-8 and anti-MMP-9 for MMPs, then subjected to fluorescence microscopy. In the images red indicates the presence of Cy5.5-c(KAHWGFTLD)NH$_2$ (SEQ ID NO. 10) or Cy5.5, green indicates MMPs, and blue indicates nuclei.

Cy5.5-c(KAHWGFTLD)NH$_2$ (SEQ ID NO. 10) bound to a variety of human tumor cells, including SKBr-3 breast cancer cells, HT1080 sarcoma cells, MDA-MB-435 breast cancer cells, MDA-MB-468 breast cancer cells, and U87 tumor cells. (See FIG. 10.) In all cell lines tested, Cy5.5-c(KAHWGFTLD)NH$_2$ (SEQ ID NO. 10) co-localized with MMPs, suggesting that binding of Cy5.5-c(KAHWGFTLD)NH$_2$ (SEQ ID NO. 10) to tumor cells is mediated in part through MMPs. (See FIG. 10.) In addition to its binding to MMP-2, MMP-8, and MMP-9, Cy5.5-c(KAHWGFTLD)NH$_2$ (SEQ ID NO. 10) may also bind to tumor cells through other MMPs or other tumor-specific binding sites because the fluorescent signal from Cy5.5-c(KAHWGFTLD)NH$_2$ (SEQ ID NO. 10) did not completely overlay the signals from MMP-2, MMP-8 and MMP-9. (See FIG. 10.) Cy5.5 alone did not display significant binding to the tumor cells. (See FIG. 10).

Figure 11:
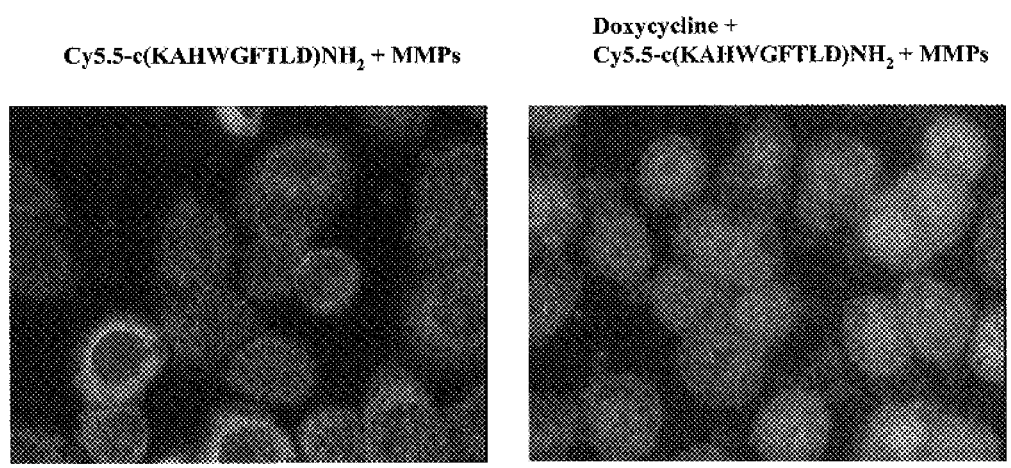
FIG. 11 shows the results of in vitro blocking assays with Cy5.5-c(KAHWGFTLD)NH$_2$ (SEQ ID NO. 10). MDA-MB-468 cells were pre-incubated with doxycycline (10 μM), a blocking agent, for 1 hour at 37° C. The cells were then incubated with Cy5.5-c(KAHWGFTLD)NH$_2$ (SEQ ID NO. 10) (10 μM) for 5 minutes. The cells were washed and stained with Sytox Green for nuclei (blue color) and with anti-MMP-2, anti-MMP-8, and anti-MMP-9 for MMPs (green color). Red indicates Cy5.5-c(KAHWGFTLD)NH$_2$ (SEQ ID NO. 10).
Figure 13:
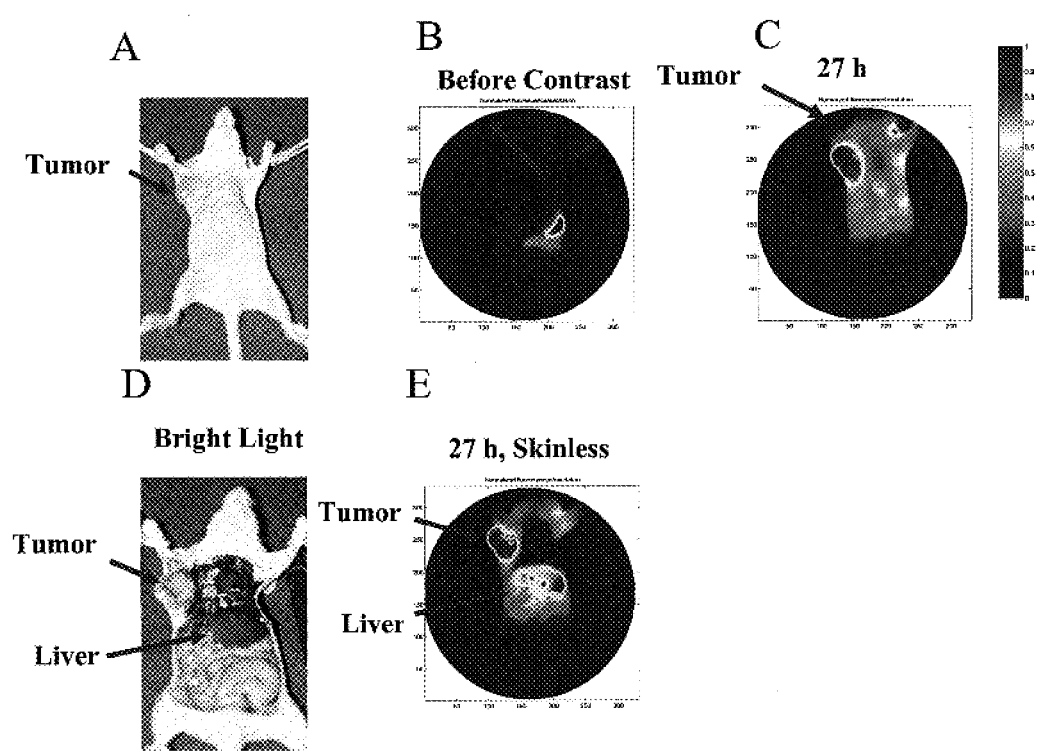
FIGS. 13A-E show representative in vivo bright light and NIR fluorescent images of subcutaneous HT1080 tumors.

An MMP-inhibitor, doxycycline (10), blocked binding of Cy5.5-c(KAHWGFTLD)NH$_2$ (SEQ ID NO. 10) to MDA-MB-468 cells. (See FIG. 11.) FIG. 13 shows a dose-dependent inhibition of the binding of Cy5.5-c(KAHWGFTLD)NH$_2$ (SEQ ID NO. 10) to U87 cells. Fluorescent intensity decreased with increasing concentration of doxycycline. However, complete blockage of binding of Cy5.5-c(KAHWGFTLD)NH$_2$ (SEQ ID NO. 10) to U87 cells was not observed even at 10-fold excess of doxycycline (100 μM), suggesting that in addition to MMPs, Cy5.5-c(KAHWGFTLD)NH$_2$ (SEQ ID NO. 10) may also bind to other specific molecular targets in U87 cells. Alternatively, the residual fluorescent signal may be attributed to nonspecific binding of Cy5.5-c(KAHWGFTLD)NH$_2$ (SEQ ID NO. 10) to tumor cells.

Tumor binding studies also showed that another cyclic Cy5.5 peptide imaging agent, c(KYHWGFTLD)NH$_2$ (SEQ ID NO. 11) also bound to tumor cells. (See FIG. 12.)

EXAMPLE 10

In Vivo Cyclic HWG Polypeptide NIR Imaging Studies

Four to six week-old athymic nude mice (18-22 g, Harlan Sprague Dawley, Inc., Indianapolis, Ind.) were housed 5 per cage with sterilized pet chow (Harlan Sprague Dawley) and sterilized water. Animals were maintained in a pathogen-free mouse colony in the Department of Veterinary Medicine at the University of Texas M.D. Anderson Cancer Center. All experiments were performed in accordance with the guidelines of the Institutional Animal Care and Use Committee. Tumor cells were harvested near confluence by incubation with 0.05% trypsin-EDTA. Cells were pelleted by centrifugation at 450×g for 5 minutes and resuspended in sterile PBS. Cells (2-3×10$^6$/animal) were implanted subcutaneously into the chest wall or the hind legs of the mice. Human PC-3 prostate tumors were obtained by intratibia injection of PC-3 cells into male nude mice. Human U87 glioma tumors were obtained by intracranial injection.

In vivo fluorescence imaging was accomplished by illuminating the animal with light from a laser diode (785 nm, 80 mW for IGC; 660 nm, 35 mW for Cy 5.5 dyes) expanded to an approximate 8 cm diameter circular area. The re-emitted fluorescent light was collected by an image intensifier (model FS9910C, ITT Night Vision, Roanoke, Va.) lens-coupled to a CCD camera (model CH350, Photometrics, Tucson, Ariz.). The imaging was designed so that the field of view could be varied from 3×3 cm to over 12×12 cm by varying the image distance of the 50 mm lens used to focus the image onto the photocathode of the intensifier. The lens was fitted with a holographic notch-plus filter (785 nm center wavelength for ICG and 660 nm center wavelength for Cy5.5 dyes; Kaiser Optical Systems, Inc., Ann Arbor, Mich.) and a bandpass filter (830 nm center wavelength for ICG, 710 nm center wavelength for Cy5.5 dyes) to reject back-scattered and reflected excitation photons. Image acquisition was accomplished using V++ software (Digital Optics, Auckland, New Zealand) and obtained images were stored in uncompressed tagged image file format (tiff). Data processing and analysis was accomplished using Matlab software (The Math Works, Inc., Natick, Mass.).

FIGS. 13A-E shows representative in vivo NIR fluorescent imaging of a HT1080 tumor inoculated subcutaneously before and at 27 hr after intravenous injection of Cy5.5-c(KAHWGFTLD)NH$_2$ (SEQ ID NO. 10) (15 nm/mouse). The imaging study was performed when the tumor reached 10 mm in diameter and was clearly visible in the bright light image. (See FIG. 13A.) An autofluorescent signal was detected in the pelvic area before contrast injection (FIG. 13B), which was later confirmed to be localized in the stomach and gut. This autofluorescence was attributable to mouse chow that contained fluorescent substances. At 27 hours after imaging agent injection, tumors were clearly visualized with minimal background signal. (See FIG. 13C.) The imaging finding in the intact animal was confirmed after the mouse was euthanized and the skin was removed. (See FIGS. 13D and 13E.) Again, the fluorescent signal from the liver and other organs was much weaker than that from the tumors. Minimal background signal is important in order to obtain excellent imaging quality with enhanced detection sensitivity.

FIG. 14 compares the NIR images of mice bearing SKBr-3 tumors 4 days after intravenous injection of Cy5.5-c(KAHWGFTLD)NH$_2$ (SEQ ID NO. 10) or Cy5.5 alone. Whereas a strong fluorescent signal was detected in the mouse injected with Cy5.5-c(KAHWGFTLD)NH$_2$ (SEQ ID NO. 10), minimal fluorescence was observed in the SKBr-3 tumor of the mouse injected with Cy5.5 alone. This suggests that targeting of Cy5.5-c(KAHWGFTLD)NH$_2$ (SEQ ID NO. 10) to the tumor was mediated through the peptide.

Similarly, MDA-MD-468 tumors and KS1767 tumors inoculated subcutaneously in the chest wall or the hind legs were clearly visualized. (See FIG. 15.)

Figure 16:
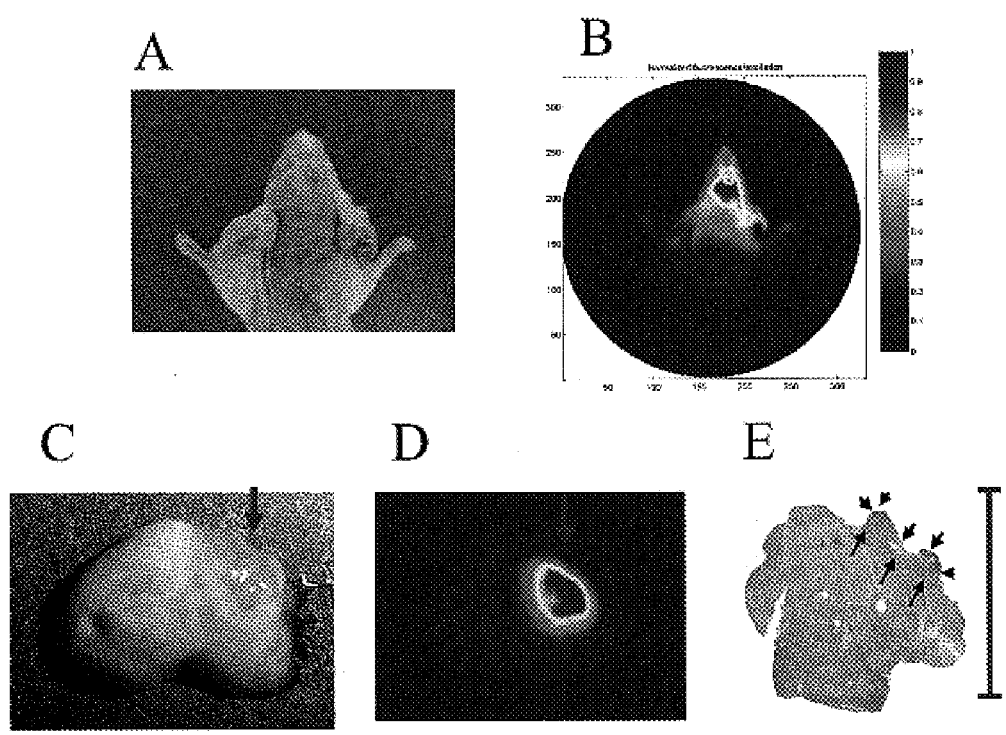

To demonstrate that NIR imaging can capture small tumors inoculated orthotopically, human glioma U87 tumor cells were injected intracranially into the brain of a nude mouse. FIG. 16 shows bright light (FIGS. 16A and 16C) and NIR fluorescence (FIGS. 16B and 16D) images of a mouse 12 days after tumor inoculation. The tumor was about 3-4 mm in diameter (FIG. 16E). In both the intact animal (FIGS. 16A and 16B) and in excised brain tissue (FIGS. 16C and 16D), binding and retention of Cy5.5-c(KAHWGFTLD)NH$_2$ (SEQ ID NO. 10) in the tumor was clearly depicted.

The ability of Cy5.5-c(KAHWGFTLD)NH$_2$ (SEQ ID NO. 10) to image small tumors was further demonstrated in mice bearing subcutaneous U87 glioma and intratibia PC-3 prostate tumors. (See FIG. 17.) The images were acquired 3 days after injection of approximately 1×10$^6$ cells of each tumor cell line. During this time period, the tumors were neither palpable nor visible in bright light images. (See FIG. 17A.) The U87 cells produced a lesion less than 2 mm in diameter. (See FIG. 17E.) PC-3 cells produced no detectable lesion as assessed by X-ray. (See FIG. 17F.) As shown in the NIR fluorescence images, both tumors were clearly visualized 24 hours and 48 hours after contract injection. (See FIGS. 17C and 17D.) The image obtained at 48 hours after contrast injection in a skinless mouse showed better imaging quality owing to elimination of reflection and absorption of light by the skin.

Finally, the specificity of Cy5.5-c(KAHWGFTLD)NH$_2$ (SEQ ID NO. 10) in tumor imaging was demonstrated by comparing the NIR images of intratibia PC-3 prostate tumors obtained with Cy5.5-c(KAHWGFTLD)NH$_2$ (SEQ ID NO. 10) and a scrambled cyclic Cy5.5-cyclic peptide imaging agent. (See FIG. 18.) The scrambled peptide used in this study, c(KHGLTWFAD)NH$_2$ (side chain-to-side chain linkage), has the same composition but different amino acid sequence compared to that of Cy5.5-c(KAHWGFTLD)NH$_2$ (SEQ ID NO. 10) (See FIG. 7.) Images of tumor-bearing mice clearly showed the presence of tumors when injected with Cy5.5-c(KAHWGFTLD)NH$_2$ (SEQ ID NO. 10), but not with Cy5.5-c(KHGLTWFAD)NH$_2$. Furthermore, no fluorescent signal was detected in the contra lateral tibia region of mice preinjected with saline followed by intravenous injection of Cy5.5-c(KAHWGFTLD)NH$_2$ (SEQ ID NO. 10), suggesting that the fluorescent signal detected in the tibia region inoculated with PC-3 cells was not a result of traumatic response to the mechanical injury of injection. This result suggests that targeted imaging of solid tumors with Cy5.5-c(KAHWGFTLD)NH$_2$ (SEQ ID NO. 10) was mediated through specific interaction between the imaging agent and tumors. A specific amino acid sequence and composition of the peptide are required for targeted delivery of the imaging agent to the tumors.

All of the compositions and/or methods disclosed and claimed herein can be made and executed without undue experimentation in light of the present disclosure. While the compositions and methods of this invention have been described in terms of specific embodiments, it will be apparent to those of skill in the art that variations may be applied to the compositions and/or methods and in the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A composition comprising at least one cyclic polypeptide of the formula $c(X_1X_2X_3HWGFTLX_4)$, wherein $X_1$, $X_2$, $X_3$ and $X_4$ may each be an L-amino acid, a D-amino acid, or a non-natural amino acid and one or more of amino acids $X_1$, $X_2$, $X_3$ and $X_4$ may be omitted, and wherein the cyclic polypeptide is cyclized through an amide bond.

2. The composition of claim 1, wherein the at least one cyclic polypeptide comprises a head-to-tail linkage.

3. The composition of claim 1, wherein the at least one cyclic polypeptide comprises a side chain-to-tail linkage.

4. The composition of claim 1 wherein the at least one cyclic polypeptide comprises a side chain-to-side chain linkage.

5. The composition of claim 1, wherein the at least one cyclic polypeptide is selected from the group consisting of: c(ATAHWGFTLβA), c(ATTHWGFTLD), c(KTTHWGFTLD), c(KTAHWGFTLD)NH2, c(KYHWGFTLD)NH$_2$, c(KAHWGFTLD)NH$_2$ and c(KAHWGFTLD).

6. The composition of claim 1, further comprising at least one imaging agent.

7. The composition of claim 6, wherein the imaging agent comprises an NIR imaging agent, wherein the NIR imaging agent is bound to the cyclic polypeptide.

8. The composition of claim 7, wherein the NIR imaging agent comprises an NIR dye.

9. The composition of claim 8, wherein the NIR dye comprises a cyanine or indocyanine derivative.

10. The composition of claim 8, wherein the NIR dye is selected from the group consisting of: Cy5.5, IRDye800, indocyanine green, indocyanine green derivatives and combinations thereof.

11. The composition of claim 8, wherein the NIR dye comprises a tetrasulfonic acid substituted indocyanine green dye or a derivative thereof.

12. The composition of claim 11, wherein the tetrasulfonic acid substituted indocyanine green comprises tetrasulfonic acid substituted indocyanine green carboxylic acid or tetrasulfonic acid substituted indocyanine green dicarboxylic acid.

13. The composition of claim 6, wherein the agent may be administered to an animal and then detected non-invasively, intraoperatively, laparoscopically or endoscopically.

14. The composition of claim 6, wherein at least one of amino acids $X_1$, $X_2$, $X_3$, or $X_4$ is tyrosine.

15. The composition of claim 14, wherein at least one tyrosine is labeled with $^{131}I$, $^{125}I$, or $^{124}I$.

16. The composition of claim 6, wherein the imaging agent comprises an MRI imaging agent.

17. The composition of claim 16, wherein the MRI imaging agent comprises Gd, Mn or iron oxide.

18. The composition of claim 6, wherein the imaging agent comprises a nuclear imaging agent.

19. The composition of claim 18, wherein the nuclear imaging agent comprises a radionuclide.

20. The composition of claim 18, wherein the radionuclide is selected from the group consisting of: $^{18}F$, $^{131}I$, $^{124}I$, $^{125}I$, $^{111}In$, $^{99m}Tc$, $^{67}Cu$, $^{64}Cu$, $^{68}Ga$ and combinations thereof.

21. The composition of claim 6, wherein the at least one cyclic polypeptide is directly covalently bound to the at least one imaging agent.

22. The composition of claim 6, wherein the at least one cyclic polypeptide is indirectly covalently bound to the at least one imaging agent.

23. The composition of claim 6, further comprising at least one additional imaging agent.

24. The composition of claim 23, wherein the imaging agents are each functional in a different imaging modality.

25. The composition of claim 6, wherein the composition is operable to detect an MMP in an animal.

26. The composition of claim 6, wherein the patient has or is suspected of having at least one condition selected from the group consisting of: cancer, osteoarthritis, intra-amniotic infection, respiratory disease having tissue destruction, bacterial meningitis, periodontal disease, rheumatoid arthritis, heart disease such as atherosclerosis and combinations thereof.

27. The composition of claim 1, further comprising at least one therapeutic agent.

28. The composition of claim 27, wherein the therapeutic agent further comprises a chemotherapeutic agent.

29. The composition of claim 28, wherein the chemotherapeutic agent is selected from the group consisting of: camptothecin, paclitaxel, doxorubicin, methotrexate and combinations thereof.

30. The composition of claim 27, wherein the therapeutic agent comprises a radionuclide.

31. The composition of claim 30, wherein the radionuclide comprises $^{131}I$ or $^{90}Y$.

32. The composition of claim 27, wherein the at least one therapeutic agent is directly covalently bound to the at least one cyclic peptide.

33. The composition of claim 27, wherein the at least one therapeutic agent is indirectly covalently bound to the at least one cyclic peptide.

34. The composition of claim 27, wherein the composition is operable to treat an MMP-related condition in an animal.

35. The composition of claim 34, wherein the condition is selected from the group consisting of: cancer, osteoarthritis, intra-amniotic infection, respiratory disease having tissue destruction, bacterial meningitis, periodontal disease, rheumatoid arthritis, heart disease such as atherosclerosis and combinations thereof.

36. The composition of claim 27, further comprising at least one additional therapeutic agent.

37. The composition of claim 6, further comprising at least one therapeutic agent.

38. The composition of claim 1, further comprising at least one linker molecule.

39. The composition of claim 38, wherein the at least one linker molecule is selected from the group consisting of: poly(L-Glutamic Acid), polyethylene glycol, an aliphatic chain, Lysine, a dual functional amino acid and combinations thereof.

* * * * *